US011400215B2

(12) United States Patent
Cowe et al.

(10) Patent No.: US 11,400,215 B2
(45) Date of Patent: Aug. 2, 2022

(54) MEDICAMENT DELIVERY DEVICE

(71) Applicant: Owen Mumford Limited, Oxfordshire (GB)

(72) Inventors: Toby Cowe, Oxfordshire (GB); Jake Mallon, Bath (GB)

(73) Assignee: Owen Mumford Limited, Oxford (GB)

( * ) Notice: Subject to any disclaimer, the term of this patent is extended or adjusted under 35 U.S.C. 154(b) by 515 days.

(21) Appl. No.: 16/317,316

(22) PCT Filed: Jul. 19, 2017

(86) PCT No.: PCT/GB2017/052122
§ 371 (c)(1),
(2) Date: Jan. 11, 2019

(87) PCT Pub. No.: WO2018/015749
PCT Pub. Date: Jan. 25, 2018

(65) Prior Publication Data
US 2019/0298925 A1 Oct. 3, 2019

(30) Foreign Application Priority Data
Jul. 19, 2016 (GB) .................................... 1612516

(51) Int. Cl.
*A61M 5/20* (2006.01)
*A61M 5/32* (2006.01)
(Continued)

(52) U.S. Cl.
CPC ...... *A61M 5/2033* (2013.01); *A61M 5/14248* (2013.01); *A61M 5/3204* (2013.01);
(Continued)

(58) Field of Classification Search
CPC ............ A61M 5/2033; A61M 5/14248; A61M 5/3204; A61M 5/1452; A61M 5/1454;
(Continued)

(56) References Cited

U.S. PATENT DOCUMENTS 5,201,210 A 4/1993 Stein, III
10,596,313 B2 * 3/2020 Gregory ................ A61M 5/288
(Continued)

FOREIGN PATENT DOCUMENTS

WO WO 2013/032841 A1 3/2013

OTHER PUBLICATIONS

Feb. 8, 2018 Transmittal of International Search Report and Written Opinion of the International Searching Authority from PCT/GB2017/052122.

*Primary Examiner* — Dung T Ulsh
(74) *Attorney, Agent, or Firm* — Quarles & Brady LLP

(57) ABSTRACT

A medicament delivery device (100) for delivery of medicament from a container (12) into an injection site through a cannula (16). The device comprises a chassis (106), a drive mechanism (400) for driving a piston member (22) along a container axis (A) to expel the medicament through the cannula (16), and a carriage (200) for retaining the container (12), the cannula (16) and the drive mechanism (400). An insertion mechanism (70, 120, 130, 504) is provided for moving the carriage (200) in an insertion direction (H) relative to the chassis (106), and a cannula bending mechanism (300) is provided for bending the cannula (16) about a bending axis (B) to substantially align at least an end part of the cannula (16) with the insertion direction (H) prior to movement of the carriage (200) in the insertion direction (H).

45 Claims, 10 Drawing Sheets

(51) Int. Cl.
*A61M 5/142* (2006.01)
*A61M 5/145* (2006.01)
(52) U.S. Cl.
CPC ......... *A61M 5/1452* (2013.01); *A61M 5/1454* (2013.01); *A61M 2005/14252* (2013.01); *A61M 2005/14256* (2013.01); *A61M 2005/206* (2013.01); *A61M 2005/208* (2013.01); *A61M 2005/2013* (2013.01); *A61M 2005/2026* (2013.01); *A61M 2005/2073* (2013.01); *A61M 2005/2086* (2013.01); *A61M 2205/14* (2013.01)
(58) Field of Classification Search
CPC ......... A61M 2005/14252; A61M 2005/14256; A61M 2005/2013; A61M 2005/2023; A61M 2005/206; A61M 2005/2073; A61M 2005/208
See application file for complete search history.

(56) References Cited

U.S. PATENT DOCUMENTS

| | | |
|---|---|---|
| 2002/0123740 A1 | 9/2002 | Flaherty et al. |
| 2008/0051714 A1 | 2/2008 | Moberg et al. |
| 2010/0268170 A1* | 10/2010 | Carrel ................. A61M 5/2033 604/198 |
| 2013/0218128 A1 | 8/2013 | Cowe |
| 2013/0324933 A1 | 12/2013 | Wilmot et al. |
| 2014/0088508 A1* | 3/2014 | Ryan ..................... A61M 5/172 604/152 |
| 2014/0194854 A1* | 7/2014 | Tsals ................. A61M 5/1456 604/513 |
| 2016/0175515 A1 | 6/2016 | McCullough |
| 2017/0368260 A1* | 12/2017 | McCullough ....... A61M 5/3158 |

* cited by examiner

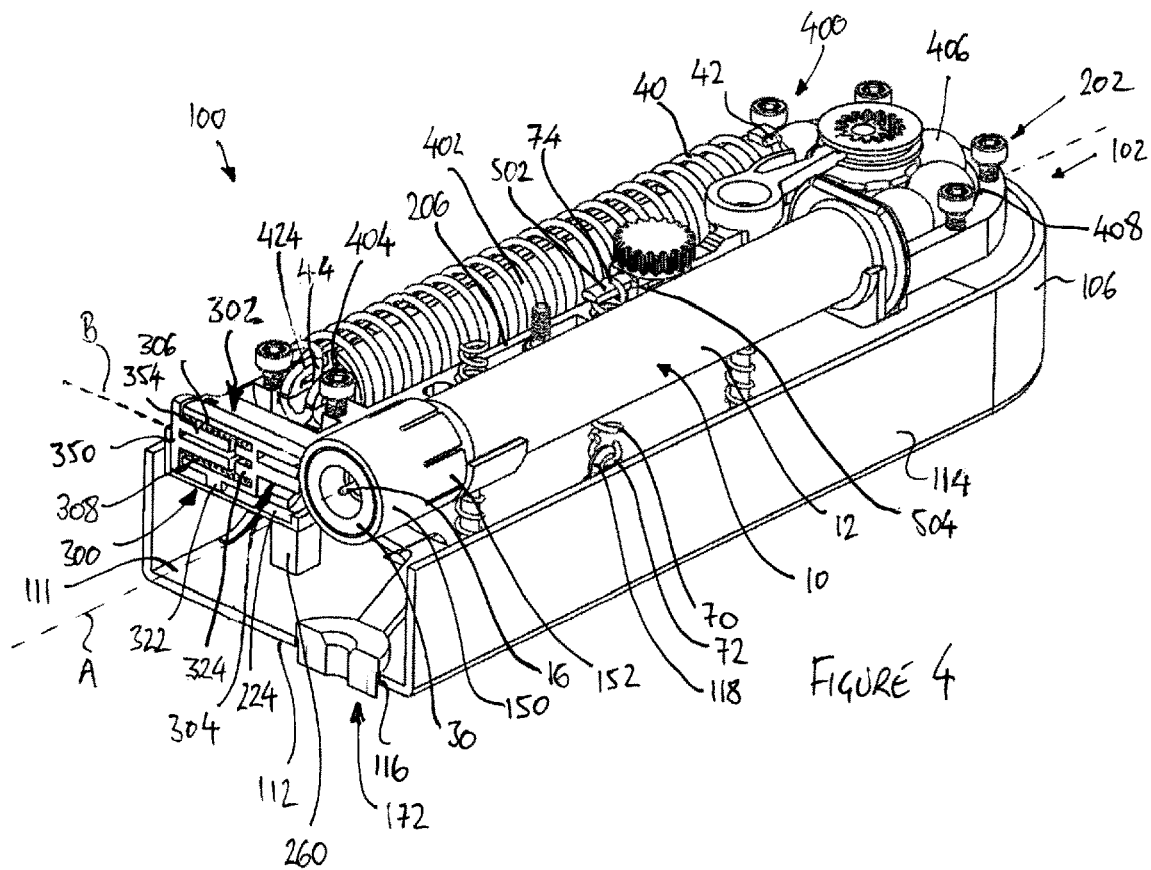
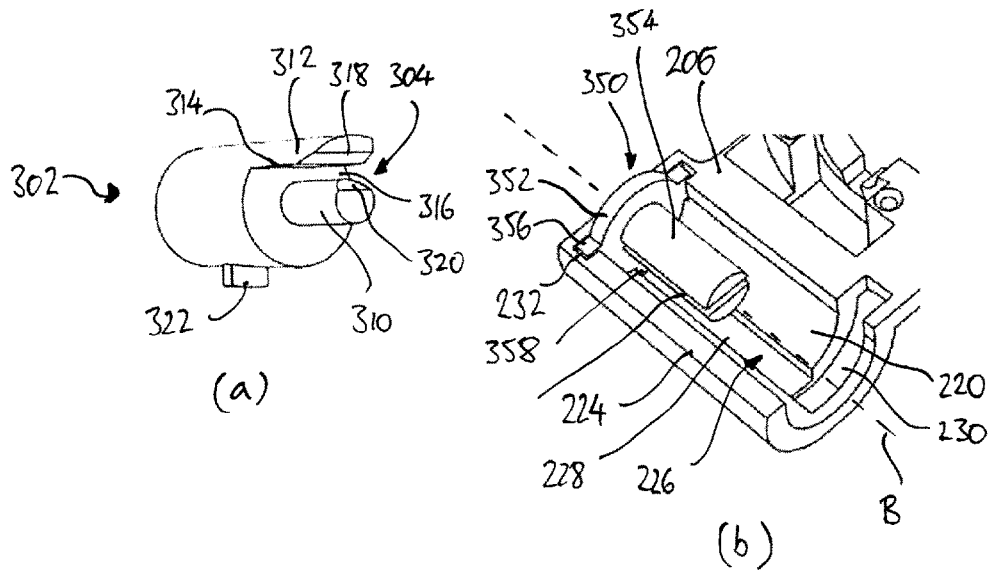
FIGURE 5

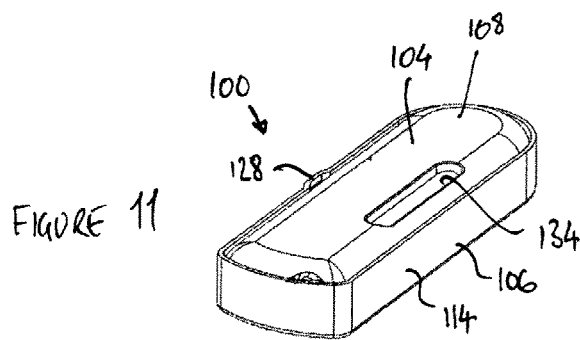
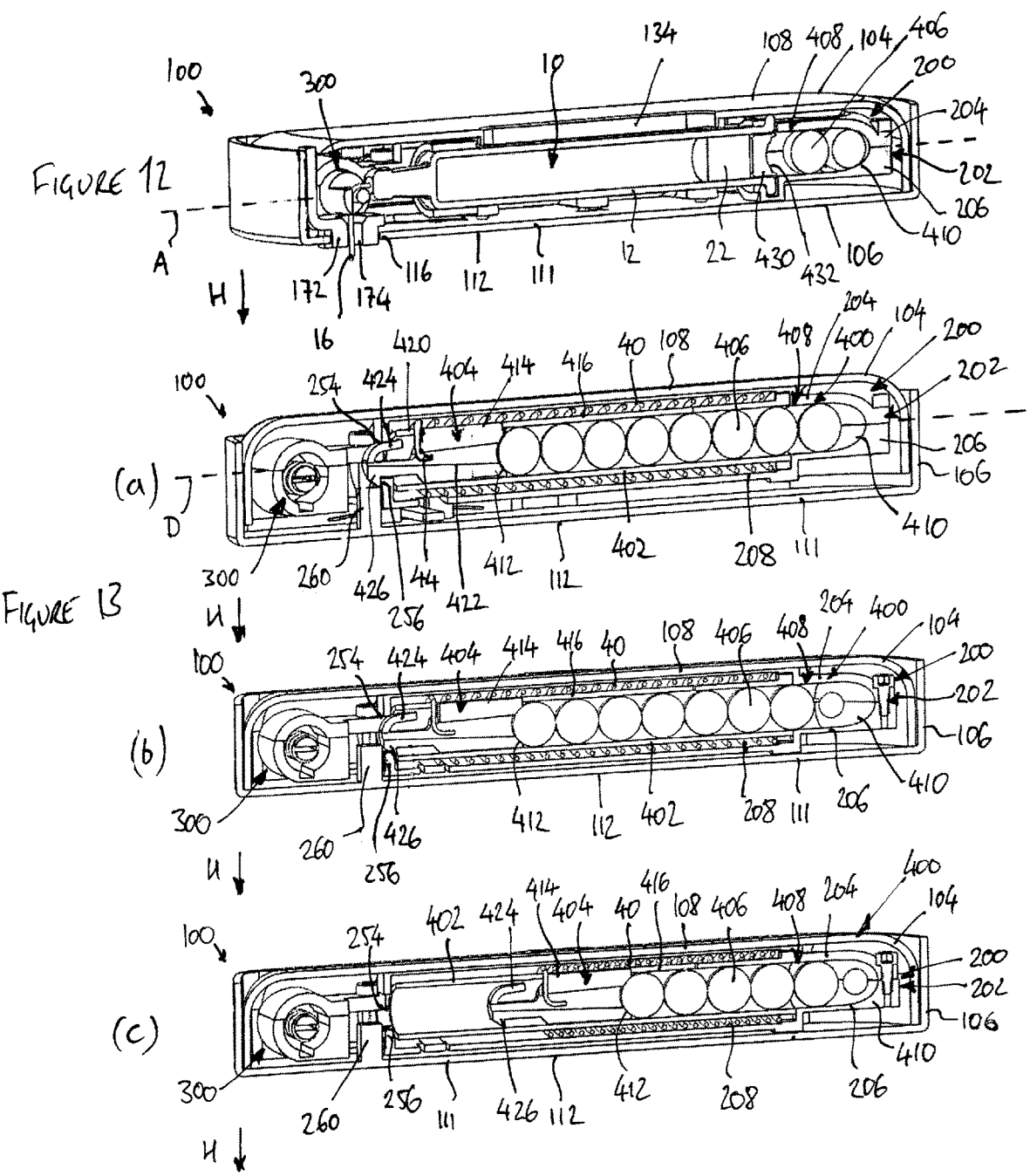

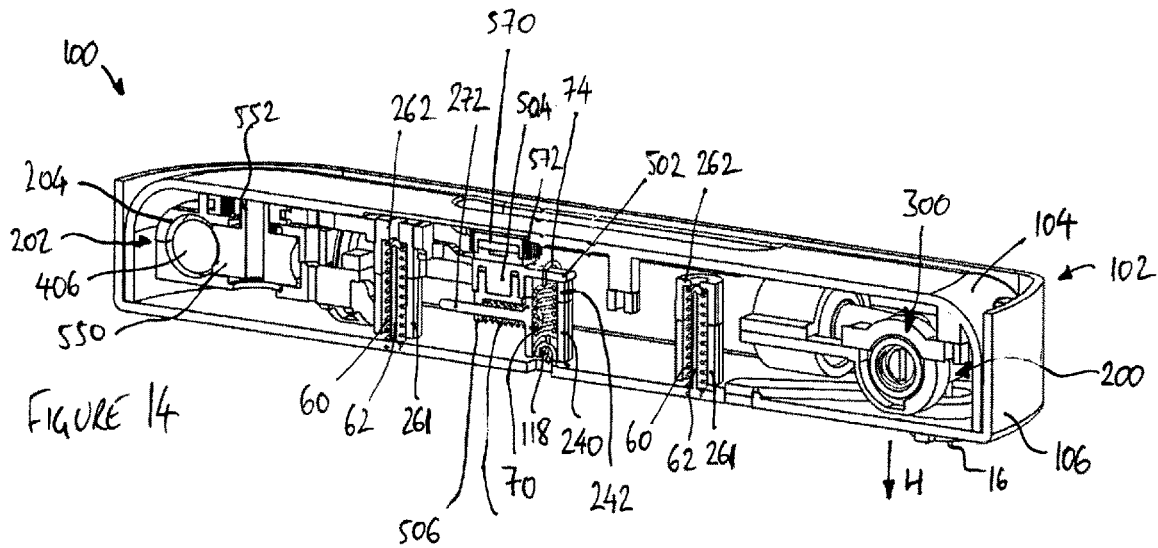
FIGURE 14
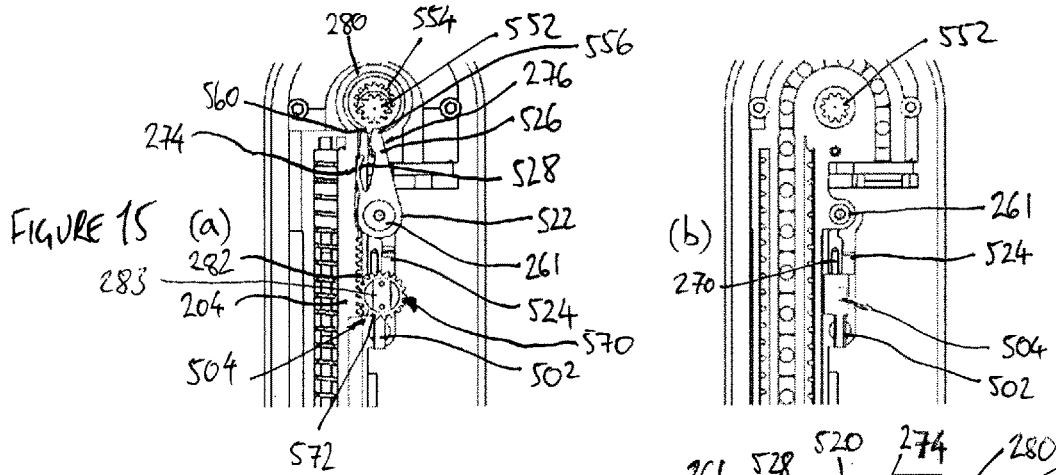
FIGURE 15 (a) (b)
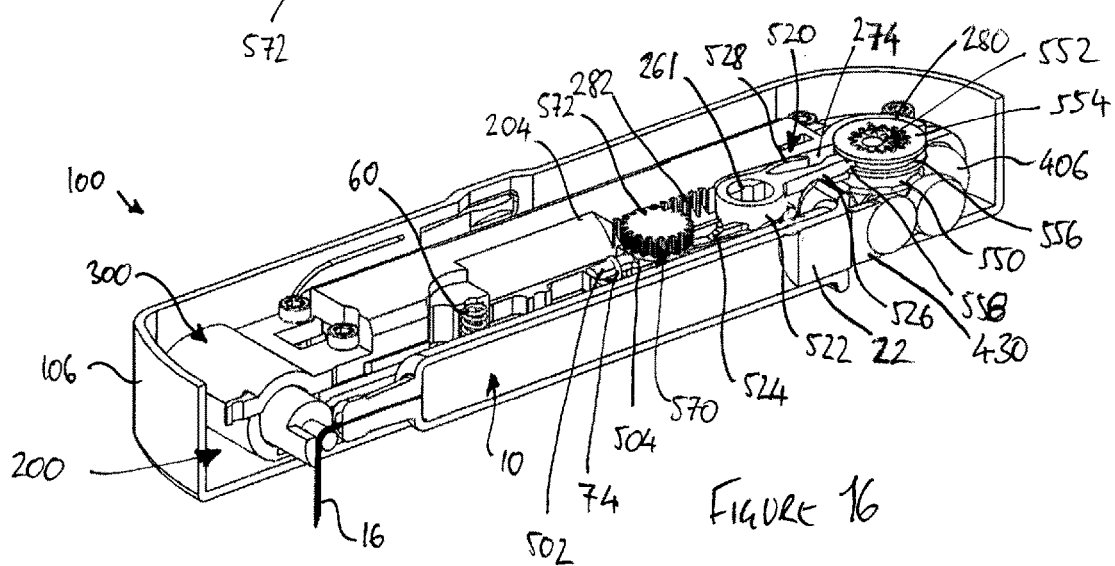
FIGURE 16

MEDICAMENT DELIVERY DEVICE

The present application is a § 371 submission of international application no. PCT/GB2017/052122, filed 19 Jul. 2017 and titled Medicament Delivery Device, which was published in the English language on 25 Jan. 2018 with publication no. WO 2018/015749 A2, and which claims the benefit of the filing date of GB 16 1612516.3 filed 19 Jul. 2016, the contents of which are incorporated herein by reference.

The present invention relates to devices suitable for the delivery of a medicament to a patient. In particular, but not exclusively, the invention relates devices in which activation of the device causes automatic insertion of a cannula to an injection site and delivery of the medicament by injection through the cannula.

Injection devices designed for automatic needle insertion and injection of a single pre-determined dose of a medicament are known in the art as auto-injectors. Such devices typically include a housing that allows the user to grip the device, a pre-filled syringe containing the medicament, and a drive mechanism. The pre-filled syringe includes a tubular glass barrel with a staked hypodermic needle at its distal end, a needle shield to protect and seal the needle, and a stopper slidably received in the barrel. One example of a pre-filled syringe of this type is available under the registered trade mark Hypak (Becton Dickinson, New Jersey, USA).

The syringe is axially movable within the housing between an initial, retracted position in which the needle is retracted in the housing, and a deployed position in which the needle projects from the end of the housing.

With the syringe in the retracted position, the distal end of the housing is closed by a cap. To prepare the device for use, the cap is removed. The cap is arranged to grip the rigid needle shield, so that removal of the cap pulls the rigid needle shield off the needle.

The distal end of the housing is then placed against the skin, and the user operates a trigger of the device, such as a button, to activate the drive mechanism. The drive mechanism typically comprises a plunger that is biased in the distal direction by a compression spring. The plunger is initially held in an initial, latched position by a latch arrangement. Upon activation of the drive mechanism, the plunger is released from the latched position and can move distally under the force of the compression spring.

Initially, release of the plunger causes the syringe to move from the retracted position into the deployed position, so that the needle pierces the skin. Subsequently, the plunger forces the stopper in the distal direction to inject the medicament.

Some auto-injector devices also include a needle retraction mechanism to withdraw the needle from the skin and retract it into the device once the medicament has been delivered. A needle retraction mechanism typically includes a retraction spring and a coupling arrangement for coupling the retraction spring to the syringe. Once coupled, the retraction spring applies a force to the syringe that acts in the proximal direction to move the needle back towards the retracted position. The coupling arrangement may be activated to retract the needle when the plunger nears or reaches the end of its distal travel.

Auto-injectors of these types can be convenient for self-administration by a patient of a measured dose of a medicament, although they may also be used by trained medical personnel. In both cases, auto-injectors typically offer increased user safety compared with traditional syringes, for example by ensuring that the needle used to deliver the medicament is shrouded before and/or after delivery of the medicament, and by the inclusion of interlock means or other safety devices to prevent accidental operation of the device.

Existing auto-injector devices can however have several drawbacks. For example, the above-described drive mechanism results in a relatively long device, since the plunger and the compression spring are disposed in a coaxial arrangement with the syringe. For some applications, it would be desirable to provide a more compact and ergonomic arrangement.

Another consequence of the linear arrangement of the device components is that the distal end of the device must be held firmly in contact with the injection site whilst the trigger is manipulated to activate the device and during subsequent delivery of the medicament. To ensure optimum needle penetration and to minimise discomfort, the body of the device should be held perpendicular to the injection site and with as little movement as possible. This may be relatively difficult for some users, such as individuals with reduced manual dexterity, impaired vision, and so on, and can be particularly problematic when injection takes place over a relatively long time period, such as when a high volume of medicament is to be delivered or when a high viscosity medicament is used.

Furthermore, the force applied to the injection site through the relatively small contact area at the distal end of the device can be relatively high, potentially leading to discomfort and to the temporary marking of the skin.

A relatively strong drive spring is usually required to ensure delivery of the medicament through the needle. This is particularly the case when the medicament has a relatively high volume, high viscosity and/or when the needle has a fine gauge. When a powerful drive spring is also used to drive insertion of the needle, the resulting impact loads on the syringe can lead to damage of the syringe and discomfort for the patient.

Also, when a needle retraction mechanism is provided, there is a risk that retraction of the needle may occur before the whole of the desired dose of medicament has been delivered. For example, variations in component dimensions due to manufacturing tolerances can give rise to variations in the point at which needle retraction is triggered, which can result in premature retraction of the needle. The relaxation of elastic strain in the device components (in particular the stopper and the plunger) can result in medicament flow through the needle even after the plunger has nominally reached the end of its stroke, resulting in a failure to deliver the complete dose if the needle is retracted too rapidly after injection. Also, if the needle is retracted before the medicament has time to dissipate into the surrounding tissue, medicament can be lost from the injection site through the puncture.

Accordingly, it would be desirable to provide an injection device that overcomes or mitigates some of the above-mentioned problems.

Against this background, in a first aspect of the present invention there is provided a medicament delivery device for delivery of medicament from a container into an injection site through a cannula, the device comprising a chassis, a drive mechanism for driving a piston member of the container along a container axis to expel the medicament through the cannula, a carriage for retaining the container, the cannula and the drive mechanism, an insertion mechanism for moving the carriage in an insertion direction relative to the chassis from a starting position, and a cannula bending mechanism for bending the cannula about a bending axis to substantially align at least an end part of the cannula with the insertion direction prior to movement of the carriage in the insertion direction.

By the incorporation of a cannula bending mechanism, the insertion direction need not be aligned with or parallel to the orientation of the cannula in a starting state of the device. Accordingly, the cannula and the container can be housed in any suitable orientation within the device, giving greater flexibility in the form factor of the device and in the selection of the medicament container and cannula arrangement. In particular, the device can be used to deliver medicament from a pre-filled container having an attached cannula or needle that is disposed coaxially with the container axis, without requiring that the insertion direction is parallel to the container axis. Thus a compact and/or low-profile device can be provided whilst using a widely-available medicament packaging in the form of a pre-filled syringe, such as a Hypak syringe, and the cost and time required to re-validate a medicament for supply in a bespoke medicament package can be avoided.

The bending mechanism preferably operates automatically during an operating sequence of the device. For example, the device may comprise a user-removable component, and removal of the user-removable component from the device may trigger operation of the bending mechanism. For example, the user-removable component may be a deshielder for removing a shield from the cannula. In this way, removal of the deshielder both exposes the cannula internally and operates the bending mechanism to bend the cannula into the correct orientation for insertion. In other examples, the removable component may a safety tab or similar removable safety element. The user-removable component may be attached to or form part of a packaging of the device, so that the user-removable component is removed upon removal of the device from the packaging.

The bending mechanism may comprise a bending member that is axially moveable along the bending axis into engagement with the cannula and turnable about the bending axis to apply a bending force to the cannula. When provided, the user-removable component may block axial movement of the bending member until the user-removable component has been removed from the device. The bending member may comprise an engagement formation for engagement with the cannula. For example, the bending member may comprise a bending surface for applying the bending force to the cannula. A former may be arranged such that the cannula conforms to a surface of the former when the bending force is applied. The bending member may comprise the former.

The bending mechanism may comprise driving means for driving axial movement of the bending member along the bending axis and/or for driving turning movement of the bending member about the bending axis. In one embodiment, the driving means comprises a spring arranged to apply an axial force and a torque to the bending member.

Guide means may be provided for preventing turning movement of the bending member about the bending axis until the bending member has moved into engagement with the cannula, and for guiding turning movement of the bending member once the bending member has engaged the cannula. The guide means may, for example, comprise a guide track and a guide element for cooperation with the guide track.

The device may comprise a contact face for contacting the injection site. The bending mechanism may be arranged to align the cannula with an opening in the contact face upon movement of the carriage in the insertion direction.

Preferably, the container axis is substantially parallel to the contact face. This provides a low-profile device, in which the height of the device (i.e. the dimension of the device normal to the contact face) is smaller than at least one width dimension of the device. With such a form factor, the device of the present invention can be more easily gripped by a user and held steady during operation, in contrast to elongate, pen-type devices in which the container axis is perpendicular to the injection site in use. Furthermore, the contact face has a relatively large area, which reduces the pressure applied to the injection site by the device and therefore lessens the risk of discomfort and skin reddening.

The bending axis may be substantially parallel to the contact face. Again, this arrangement contributes to the low-profile form factor of the device. The bending axis may be substantially perpendicular to the container axis.

The device may comprise an interlock arrangement for preventing operation of the insertion mechanism until the cannula has been aligned with the insertion axis. The interlock arrangement may further prevent operation of the insertion mechanism until the device is in contact with the injection site. In this way, the interlock arrangement acts to ensure that the device is operated in the correct sequence.

In one embodiment, the interlock arrangement is switchable from a first position in which operation of the insertion mechanism is prevented to a second position in which operation of the insertion mechanism is possible. When a user-removable component is provided, the interlock arrangement may be held in the first position by the user-removable component, and the interlock arrangement may be switchable to the second position after removal of the user-removable component.

Sensor means may be provided for switching the interlock arrangement to the second position when a contact face of the device is placed against the injection site. The sensor means may be disposed on the contact face, when provided, and may be moveable from a projecting position to a retracted position upon application of the contact face to the injection site.

The insertion mechanism may comprise a latch arrangement for holding the carriage in the starting position, and a trigger component operable to release the latch arrangement to allow movement of the carriage in the insertion direction. Operation of the trigger component may be blocked by the interlock arrangement when the interlock arrangement is in the first position.

The drive mechanism may comprise a drive member that is movable with respect to the carriage upon activation of the drive mechanism, drive means for applying a driving force to the drive member along a drive axis and force transmission means for transmitting the driving force from the drive member to the piston member. The drive axis may be substantially parallel to and spaced from the container axis. This arrangement provides a compact drive mechanism that can be readily accommodated in a device with a low profile form factor.

The drive means may be arranged around or alongside at least part of the force transmission means. For example, the drive means may comprise a tension spring arranged concentrically around at least part of the force transmission means. This provides a particularly space-efficient design. To improve further the compactness of the arrangement, the drive means may be disposed alongside the container. A first end of the force transmission means may be aligned with the drive axis and a second end of the force transmission means may be aligned with the container axis. To this end, the force transmission means may be guided in a guide track associated with the carriage. In one embodiment, the force transmission means comprises an array of balls.

Preferably, operation of the drive mechanism to start delivery of the medicament occurs automatically after the cannula has been inserted in the injection site by movement of the carriage in the insertion direction. Thus, the drive mechanism may be activated in response to the carriage reaching an activation position during movement of the carriage in the insertion direction. In one embodiment, a drive trigger associated with the chassis is provided for activating the drive mechanism when the carriage reaches the activation position. Preferably, the activation position is reached before the end of movement of the carriage in the insertion direction.

The device may comprise a retraction mechanism for moving the carriage with respect to the chassis in a retraction direction opposite to the insertion direction to withdraw the cannula after delivery of the medicament. For example, the insertion mechanism may comprise an insertion spring for biasing the carriage in the insertion direction, and the retraction mechanism may comprise a coupling arrangement for releasably coupling the insertion spring to the carriage and for decoupling the insertion spring from the carriage upon activation of the retraction mechanism. Once the insertion spring has been decoupled, the carriage is free to move in the retraction direction. To this end, the retraction mechanism may comprise a retraction spring for driving movement of the carriage in the retraction direction to retract the cannula after delivery of the medicament. The insertion spring is preferably non-parallel to the container axis. For example, the insertion spring may extend in a perpendicular direction with respect to the container axis. Because the insertion spring is not also responsible for driving the piston member to deliver the medicament, the insertion spring can be selected to provide an optimum insertion force that minimises impact loads.

When a retraction mechanism is provided, it is important that the retraction mechanism can be reliably activated to withdraw the cannula from the injection site. Thus the drive mechanism may be operable to move the piston member through a delivery stroke in the container, and the retraction mechanism may be activated by the drive mechanism before the end of the delivery stroke. To ensure complete delivery of the medicament and to allow time for the medicament to dissipate in the injection site, the insertion spring may be decoupled from the carriage after a delay time has elapsed following activation of the retraction mechanism.

The coupling arrangement may comprise a coupling member that is moveable with respect to the carriage to decouple the insertion spring from the carriage. The coupling arrangement may further comprise a retaining member arranged to prevent movement of the coupling member before activation of the retraction mechanism and to allow movement of the coupling member upon activation of the retraction mechanism.

The coupling member may be biased for movement with respect to the chassis, for example by a coupling spring. The coupling member may be guided for movement in a direction parallel to the container axis. The coupling member may comprise a pin for engagement with an end termination of the insertion spring. For example, the insertion spring may be a tension spring with a hooked or looped end termination for engagement with the pin, and the pin may slide free of the end termination upon movement of the coupling member to decouple the spring. The chassis may include a guide to prevent displacement of the insertion spring whilst the coupling member is disengaging from the spring.

The device may comprise damping means for retarding movement of the coupling member after activation of the retraction mechanism, so that, after activation of the retraction mechanism, a time delay elapses before the insertion spring is decoupled from the coupling member. The damping means may comprise a viscous damper. In one embodiment, a rack is arranged for engagement with a toothed rotary element of the damping means, such that movement of the coupling member with respect to the carriage causes rotation of the rotary element. The rotary element may rotate against a damping fluid to retard movement of the coupling member. For example, the rotary element may drive a vane within a chamber containing the damping fluid. Preferably, the rotary element is moveable with the coupling member, and the rack is associated with the carriage.

The device may comprise a wheel that is driven for rotation with respect to the carriage by the drive mechanism. The retraction mechanism may be activated upon rotation of the wheel through a pre-defined angle. For example, the wheel may comprise an actuator element for cooperation with the retaining element upon rotation of the wheel through the pre-defined angle, thereby to cause release of the coupling member. The actuator element may, for example, be a tab or tooth on the wheel. The wheel may be driven for rotation by a sprocket that is, in turn, driven by the drive mechanism. For example, the sprocket may be driven by the force transmission means of the drive mechanism. The wheel may be driven by the sprocket through a gear train, for example to allow the sprocket to rotate through a larger angle than the wheel during operation of the drive mechanism. In one embodiment, the wheel comprises an annular gear driven by a pinion attached to the sprocket. The retaining element may comprise a lever arranged to pivot with respect to the carriage upon cooperation with the actuator element, thereby to release the coupling member.

According to a second aspect of the invention, there is provided a medicament delivery device for delivery of medicament from a container into an injection site through a cannula, the device comprising a contact face for placement against the injection site, a drive mechanism for driving a piston member of the container along a container axis to expel the medicament through the cannula, the container axis being substantially parallel to the contact face, an insertion mechanism operable to move the cannula in an insertion direction to extend the cannula through an aperture in the contact face, sensor means for detecting if the contact face is in contact with the injection site, and interlock means coupled to the sensor means and switchable from a first state in which operation of the insertion mechanism is prevented to a second state in which operation of the insertion mechanism is possible in response to the contact face being placed against the injection site.

In the second aspect of the invention, a device with a low-profile form factor is provided, in which unintentional operation of the device is avoided by provision of the interlock means. Instead, the injection operation of the device can only commence once the contact face of the device has been correctly placed against the injection site.

Preferably, the sensor means comprises a sensing element disposed at the contact face and arranged to contact the injection site when the contact face is placed against the injection site. For example, the sensing element may be biased to project from the contact face, and the sensing element may be movable into a retracted position when the contact face is placed against the injection site.

In one arrangement, the sensing element is disposed in the aperture in the contact face, and the sensing element comprises an opening to allow extension of the cannula through the aperture upon operation of the insertion mechanism.

The device may comprise a trigger arrangement that is moveable to operate the insertion mechanism, and the interlock means may comprise a trigger blocking element for blocking movement of the trigger arrangement when the interlock means is in the first state. The interlock means may comprise a beam member for coupling the sensor means to the trigger blocking element. The beam member may be arranged to pivot upon switching of the interlock means from the first state to the second state. In one embodiment, the trigger arrangement comprises a trigger lever arranged to pivot to operate the insertion mechanism. The contact face may comprise a base of the device, and the trigger arrangement may be disposed on a side wall of the device. The device may comprise a chassis that defines the contact face, and the trigger arrangement may be disposed on a side wall of the chassis. When provided, the beam member and/or the trigger lever may be arranged to pivot with respect to the chassis.

Preferably, the device further comprises a user-removable component, such as a deshielder for removing a shield from the cannula, and the user-removable component may prevent switching of the interlock means from the first state to the second state until the user-removable component has been removed. Thus, the user-removable component provides additional security against unintentional operation of the device. The user-removable component is conveniently removable along the container axis.

The device may further comprise a carriage for retaining the container, the cannula and the drive mechanism, and the carriage may be biased for movement in the insertion direction relative to the contact face upon operation of the insertion mechanism. The device may further comprise a retraction mechanism for moving the carriage with respect to the contact face in a retraction direction opposite to the insertion direction to withdraw the cannula after delivery of the medicament.

In a third aspect, the present invention provides a medicament delivery device for the delivery of medicament from a container through cannula, the container having a piston member for containing the medicament within the container, the device comprising a chassis, a carriage for retaining the cannula, an insertion mechanism operable to apply an insertion force to the carriage to move the carriage in an insertion direction with respect to the chassis from a starting position to an insertion position, and a drive mechanism operable to move the piston member through a delivery stroke in the container to expel medicament through the cannula. The device further comprises a retraction mechanism for moving the carriage in a retraction direction opposite to the insertion direction and arranged for activation by the drive mechanism, and a time delay mechanism for providing a delay time between the end of the delivery stroke and the movement of the carriage in the retraction direction.

The retraction mechanism may comprise a coupling member for releasably coupling the insertion force to the carriage and for decoupling the insertion force from the carriage upon activation of the retraction mechanism. The coupling member may be movable with respect to the carriage upon activation of the retraction mechanism. For example, the coupling member may be driven by an actuator, which may comprise a spring.

The time delay mechanism may comprise damping means for retarding operation of the retraction mechanism to provide the delay time. For instance, the damping means may retard movement of the coupling member after activation of the retraction mechanism The damping means may comprise a viscous damper or dashpot. The damping means may comprise a rotary element that is cooperable with a linear element, such that movement of the coupling member with respect to the carriage causes rotation of the rotary element. The rotary element may rotate against a damping fluid to retard movement of the coupling member. For example, the rotary element may drive a vane within a chamber containing the damping fluid. The rotary element may be moveable with the coupling member, and the rack may be associated with the carriage. Any damping means suitable for slowing the movement of the coupling member could be used. For example, a linear viscous damper could be used.

In any aspect of the invention, the cannula may be substantially coaxial with the container axis in a starting state of the device. The cannula may comprise a needle attached to an end of the container. For example, the container may comprise a syringe body of a pre-filled syringe.

Preferred and/or optional features of each aspect of the invention may also be used, alone or in appropriate combination, in the other aspects of the invention also.

Embodiments of the present invention will now be described, by way of example only, with reference to the accompanying drawings, in which like reference numerals are used for like features, and in which:

FIG. 4 is a perspective view of the device of FIG. 1 sectioned on a vertical plane containing a needle bending axis B, with a cover part and an upper carriage body part omitted;

Figure 1:
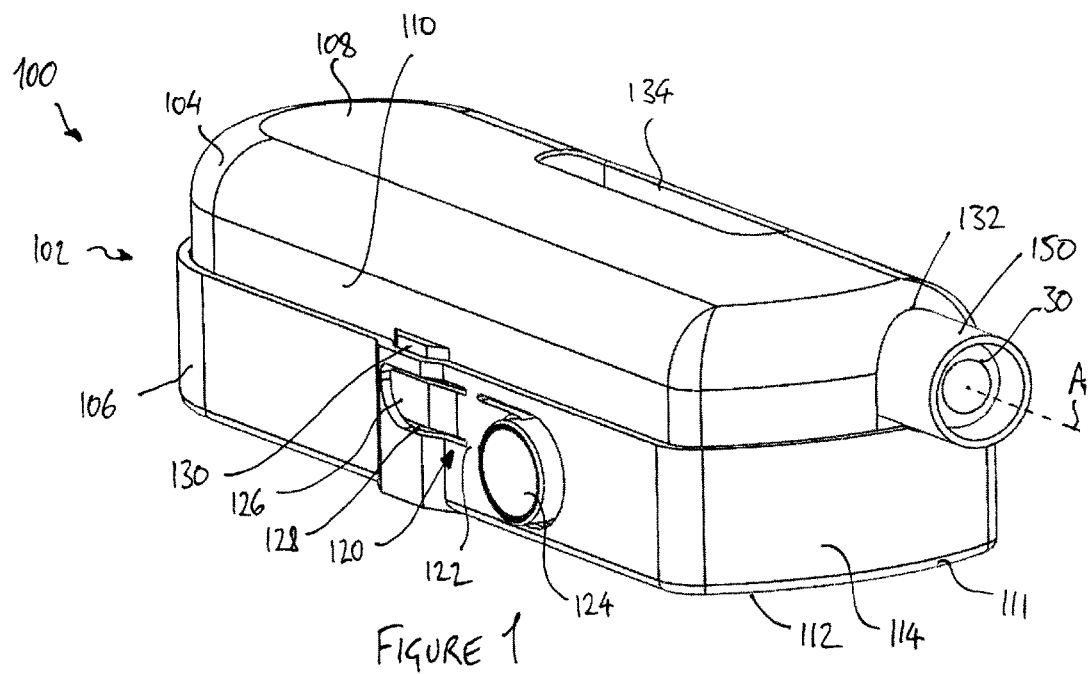
FIG. 1 is a perspective view of a device according to the present invention in a starting state.
Figure 6:
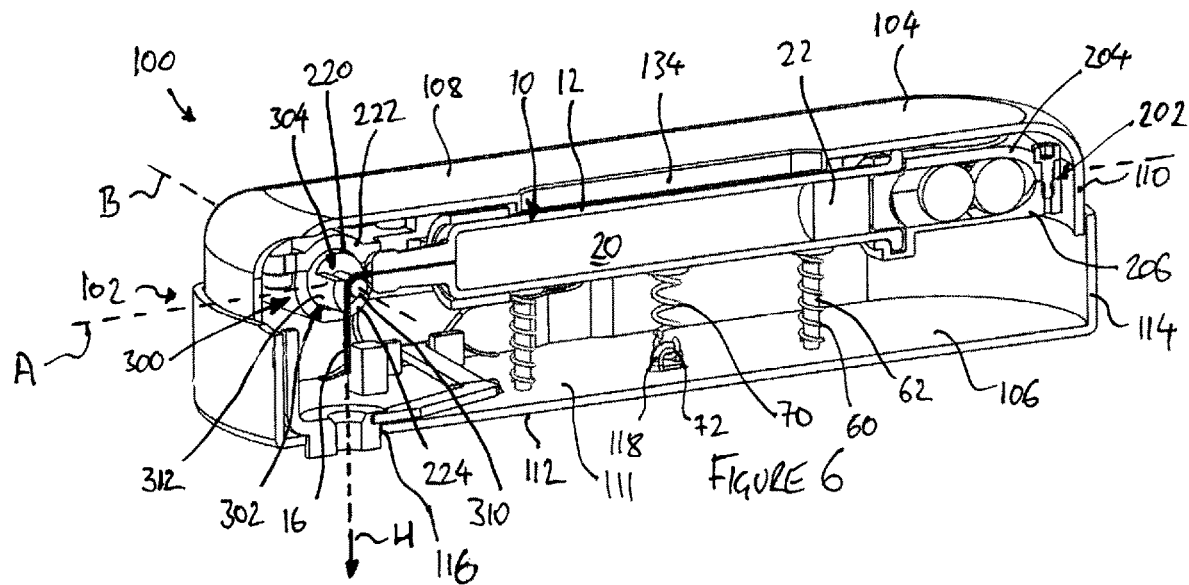
Figure 7:
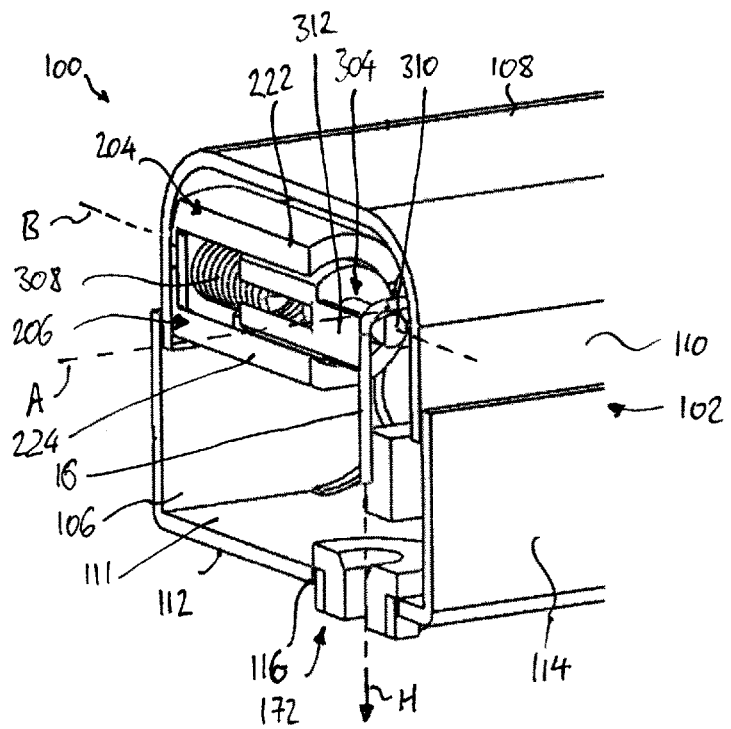

FIGS. 5(a) and 5(b) are perspective views of a needle bending element and part of a lower carriage body part, respectively, of the device of FIG. 1;

FIG. 6 is a perspective view of the device of FIG. 1 sectioned on a vertical plane containing the container axis A after removal of a needle shield;

FIG. 7 is a perspective view of part of the device of FIG. 1 sectioned on a vertical plane perpendicular to the container axis A after removal of the needle shield;

FIGS. 8(a) and 8(b) are sectioned perspective views showing components of an interlock mechanism of the device of FIG. 1, when the contact face is spaced from and applied to an injection site, respectively;

FIGS. 9(a) and 9(b) are perspective views of the device of FIG. 1 sectioned on a vertical plane containing the container axis A, showing a contact face of the device spaced from and applied to an injection site, respectively;

FIGS. 10(a) to 10(c) are perspective views of the device of FIG. 1 sectioned on a vertical plane perpendicular to the container axis A, showing a sequence of steps to insert the needle in the injection site;

FIG. 11 is a perspective view of the device of FIG. 1 after insertion of the needle;

FIG. 12 is a perspective view of the device of FIG. 1 sectioned on a vertical plane containing the container axis A, after insertion of the needle;

FIGS. 13(a) to 13(c) are perspective views of the device of FIG. 1 sectioned on a vertical plane containing a drive axis D, showing a sequence of steps to deliver a medicament;

FIG. 14 is a perspective view of the device of FIG. 1 sectioned on a central vertical plane after insertion of the needle;

FIGS. 15(a) and 15(b) are cross-sectional views of part of the device of FIG. 1 on first and second horizontal planes, respectively;

FIG. 16 is a cut-away view of the device of FIG. 1 after insertion of the needle and with a cover part omitted to show components of a retraction mechanism; and FIGS. 17(a) to 17(f) are perspective views of the device of FIG. 1 sectioned on a vertical plane containing the container axis A, showing a sequence of steps for medicament delivery and needle retraction.

Throughout the following description, the terms "top", "bottom", "upper", "lower", "up", "down", "horizontal", "vertical" and related terms are used with reference to the orientation of the device as illustrated in the accompanying drawings. It should however be appreciated that these terms are not to be considered to be limiting, and that the device could be used in any suitable orientation.

Figure 2:
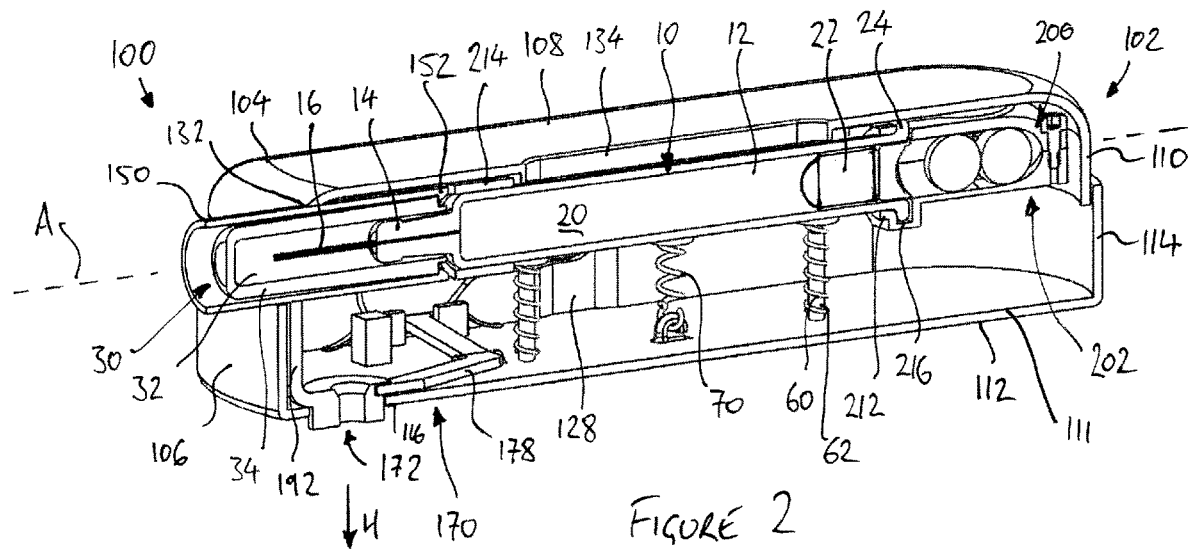
FIG. 2 is a perspective view of the device of FIG. 1 sectioned on a vertical plane containing a container axis A.

FIGS. 1 and 2 show a device 100 according to the invention in a starting state. The device 100 comprises a housing 102 formed from an upper housing part or cover 104 and a lower housing part or chassis 106. The cover 104 and the chassis 106 fit together to enclose an interior of the device 100, with the cover 104 shaped and dimensioned to slide with respect to the chassis 106 in a telescoping arrangement.

The cover 104 includes a top face 108 and a downwardly-projecting skirt 110 arranged around the periphery of the top face 108. The chassis 106 includes a baseplate 111 that is bordered by an upstanding wall 114. With the cover 104 and the chassis 106 fitted together and with the device in the starting state of the device 100, the top face 108 and the baseplate 111 are parallel and a top part of the upstanding wall 114 overlaps with a bottom part of the skirt 110 as shown most clearly in FIG. 2. The underside of the baseplate 111 of the chassis 106 forms a contact face 112 of the device 100 that is held against an injection site in use, as will be described below.

Referring to FIG. 1, a trigger lever 120 is disposed on a side of the device 100. In this example, the trigger lever 120 is formed in the wall 114 of the chassis 106 by way of suitable cut-outs. The trigger lever 120 is attached to the wall 114 by a pair of stays 122, arranged on opposite upper and lower sides of the trigger lever 120 along a vertical axis.

A first end of the trigger lever 120 is enlarged to form a generally circular trigger button 124. A second end of the trigger lever 120 forms a blocking member 126. As will be explained in more detail below, during operation of the device 100, the trigger button 124 can be pushed towards the interior of the housing 102 to pivot the trigger lever 120 about the vertical axis defined by the stays 122. Pivoting of the trigger lever 120 results in twisting of the stays 122, generating a torsional restoring force that urges the trigger lever 120 back to a neutral position if the trigger button 124 is released.

Adjacent to the trigger lever 120, a portion of the wall 114 of the chassis 106 is deflected outwardly to define a vertical channel or recess 128 that opens to the interior of the housing 102 (as can be seen most clearly in FIG. 2). An outwardly-projecting stop 130, visible in FIG. 1, is disposed on the skirt 110 of the cover 104. The stop 130 is positioned to be disposed at the top of the recess 128 when the device 100 is in the starting state. When the trigger lever 120 is in the neutral position, the blocking member 126 extends into the recess 128 to prevent downward movement of the stop 130, and hence downward movement of the cover 104 with respect to the chassis 106 cannot occur.

Figure 3:
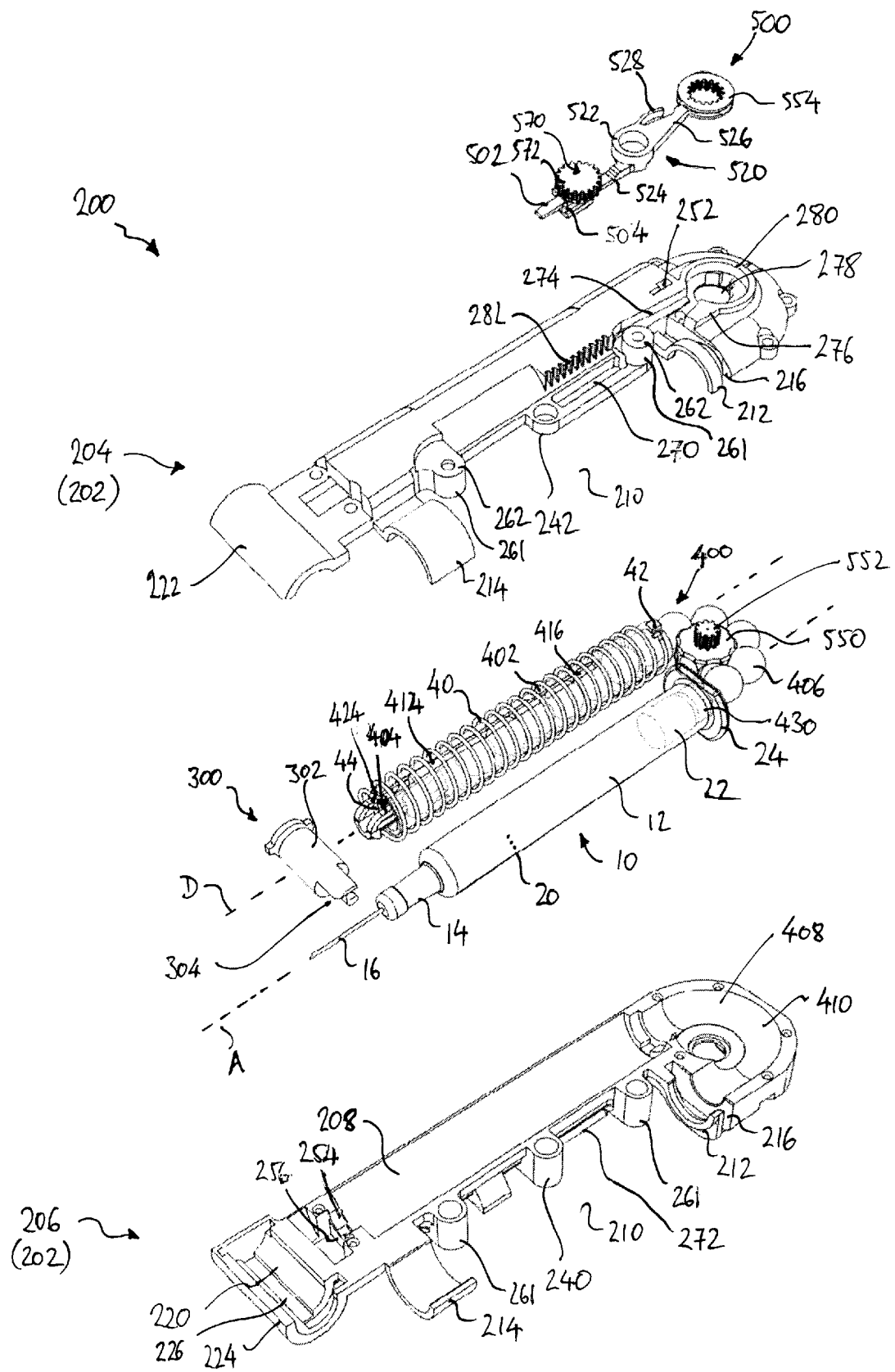
FIG. 3 is an exploded view showing a carriage assembly of the device of FIG. 1.

A carriage assembly 200 is housed in the interior of the housing 102. FIG. 2 shows the carriage assembly 200 in situ in the housing 102, and FIG. 3 shows an exploded view of the carriage assembly 200. The carriage assembly 200 includes a medicament container in the form of a pre-filled syringe 10. The syringe 10 comprises a generally tubular glass body or barrel 12 that defines a container axis A. At one end, the barrel 12 is formed into a reduced-diameter end portion 14 that carries a staked cannula in the form of a hypodermic needle 16. The barrel 12 is filled with a quantity of medicament 20 and is closed by a stopper 22 that is slidably received in the barrel 12 to act as a piston member. An outwardly-projecting flange 24 is provided at the end of the barrel 12 opposite the needle 16.

A removable needle shield 30 (see FIG. 2, not shown in FIG. 3) is provided to seal the needle 16 to maintain the sterility of the needle 16 and the medicament 20 in the container 10. The shield 30 comprises an elastomeric insert 32 and a rigid cap 34, and is known in the art as a rigid needle shield. In the starting state of the device, the shield 30 is attached to the end portion 14 of the barrel 12, and extends out of the housing 102 through an aperture 132 in the cover 104. The syringe 10 may be of a type generally known in the art, for example as available under the registered trade mark Hypak (Becton Dickinson, New Jersey, USA), and may be supplied in pre-filled form with the needle shield 30 fitted. A window 134 in the cover 102 allows part of the syringe barrel 12 to be viewed from outside the device 100.

The device 100 also includes a removable deshielder cap or sleeve 150 that is concentrically arranged around the needle shield 30. The sleeve 150 is generally tubular, and is provided with clips or barbs 152 on the inside wall of the sleeve 150, adjacent to its inner end. The barbs 152 are arranged to engage the cap 34 of the needle shield 30. An outside end part of the sleeve 150 extends through the aperture 132 in the cover 104 and beyond the end of the needle shield 30 to protrude out of the housing 102.

During operation of the device 100, the sleeve 150 can be gripped and pulled away from the housing 102 along the container axis A. In this way, the sleeve 150 comprises a user-removable component of the device 100. As the sleeve 150 is withdrawn from the housing 102, the barbs 152 engage with the cap 34 of the needle shield 30 so that the needle shield 30 is pulled off the syringe 10 and removed from the device 100.

Referring again to FIG. 3, the carriage assembly 200 includes a carriage body 202 having an upper carriage body part 204 and a lower carriage body part 206 that fit together in a clamshell arrangement to retain the syringe 10 and to house a cannula or needle bending mechanism 300 and a drive mechanism 400 of the device 100. The carriage body 202 is attached to the cover 104 by means of screws or other suitable fixings (not shown), so that the carriage assembly 200 and the cover 104 are fixed together.

The syringe 10 is arranged in a cut-out region 210 of the carriage body 202. Each carriage body part 204, 206 includes a first ring part 212 and a second ring part 214 that extend into the cut-out region 210 to retain the syringe 10. Each of the first ring parts 212 is spaced from an end of the cut-out region 210 to define a slot 216. When assembled, the flange 24 of the syringe 10 fits into the slot 216 to prevent movement of the syringe 10 with respect to the carriage body 202. The second ring parts 214 form a collar around the syringe body 12, adjacent to the end portion 14, to provide further support for the syringe 10.

With the syringe 10 mounted to the carriage body 202, the needle 16 of the syringe 10 is aligned with the container axis A. It is therefore necessary to bend the needle 16 so that the end of the needle points towards the contact face 112 of the device 100 before an injection can take place. To this end, the needle bending mechanism 300 is operable to bend the needle 16 automatically upon removal of the deshielder sleeve 150 from the device.

Referring to FIGS. 3 to 5, the needle bending mechanism 300 comprises a needle bending member 302 that is mounted laterally with respect to the syringe 10. The bending member 302 is slidably mounted in a generally cylindrical space 220 formed in an end portion of the carriage body 202. The cavity 220 is defined between upper and lower part-tubular holder sections 222, 224 of the upper and lower carriage body parts 204, 206, respectively.

The bending member 302 is guided for axial movement with respect to the carriage body 202 along a bending axis B. Viewed from the top of the device, the bending axis B lies at right angles to the container axis A, although the bending axis B does not intersect the container axis A.

The bending member 302 is generally cylindrical. A forward end of the bending member 302, closest to the container axis A, is shaped to provide a needle engaging formation 304. A blind bore 306 extends from the rear end of the bending member, opposite the forward end, to accommodate a needle bending spring 308 and part of a spring retainer 350, as will be described below.

Referring particularly to FIG. 5(a), which shows the bending member 302 in isolation, the needle engaging formation 304 includes a generally cylindrical, rod-like arbor or former 310 that extends from the forward end of the bending member 302 along the bending axis B, and a bending arm 312 that extends from the forward end of the bending member 302 parallel to the former 310 and offset from the bending axis B.

The outer surface of the bending arm 312 is part-cylindrical and continuous with the outer surface of the remainder of the bending member 302, while the inner surface 314 of the bending arm 312, closest to the former 310, comprises a flat surface, referred to hereafter as a bending surface. The former 310 and the bending surface 314 of the bending arm 302 are spaced apart to define a slot 316 therebetween. The slot 316 has an open end at the forward end of the bending member 302.

As will be explained in more detail below, in use of the device 100, the bending member 302 moves into a cooperating position with respect to the needle 16 in which the needle 16 is received in the slot 316. To guide the needle 16 into the slot 316, the bending surface 314 of the bending arm 312 is chamfered or bevelled to form an inclined ramp 318 adjacent to the open end of the slot 316. The side of the former 310 that faces the bending arm 312 is similarly chamfered or bevelled at its forward end to form a corresponding inclined ramp 320 adjacent to the open end of the slot 316.

The bending member 302 is also provided with a guide pin 322 that projects radially outwards from the cylindrical outside surface of bending member 302. Referring additionally to FIG. 5(b), which shows the lower holder section 224 with the spring retainer 350 in place but with the bending member 302 and the spring 308 omitted, a guide track 226 for the guide pin 322 is provided in the lower holder section 224. The guide track 226 comprises a generally L-shaped channel formed in the upper side of the lower carriage body part 206. The guide track 226 has a rear portion 228 that extends parallel to the bending axis B, and a forward portion 230 that extends part-way around the circumference of the cavity 220.

The spring retainer 350, shown most clearly in FIG. 5(b), comprises an end plate 352 and an elongate guide rod 354 that extends from the centre of the end plate 352 along the bending axis B. A pair of diametrically-opposed, radially-extending key elements 356 are provided on the periphery of the end plate 352 to engage with corresponding slots 232 formed at the end of the cavity 220 in the lower holder section 224. A further key element 358 extends downwardly from the periphery of the end plate 352 to engage with the linear rear portion 228 of the guide track 226. In this way, the key elements 356, 358 prevent linear and rotational movement of the spring retainer 350 with respect to the carriage body 202.

Referring back to FIG. 4, when assembled, the needle bending spring 308 is disposed concentrically around the guide rod 354. The guide rod 354 is slotted along its length to receive a rear end termination (not shown) of the needle bending spring 308. A similar slotted guide rod 324 is provided at the internal end of the blind bore 306 of the bending member 302 to receive a forward end termination (not shown) of the needle bending spring 308.

The needle bending spring 308 acts both in compression and torsion, and in this example comprises an open-coil helical spring. During assembly, the needle bending spring 308 is compressed and twisted so that the needle bending spring 308 applies both an axial force and a torque to the bending member 302.

In the starting state of the device 100, the bending member 302 is held in a retracted position by the deshielder sleeve 150. In the retracted position, the guide pin 322 of the bending member 302 is within the linear rear portion 228 of the guide track 226, so that turning movement of the bending member 302 about the bending axis B is prevented and the torsion in the needle bending spring 308 is maintained by virtue of the engagement between the end terminations of the spring 308 with the slotted guide rods 324, 354. The bending member 302 is spaced away from the container axis A and separated from the needle 16 by the deshielder sleeve 150 and the needle shield 30.

When the deshielder sleeve 150 is removed during operation of the device, the bending member 302 is free to move axially along the bending axis B under the force applied by the needle bending spring 308. The needle engaging formation 304 thus moves into an overlapping position with respect to the container axis A, so that the needle 16 is guided into the slot 316 between the former 310 and the bending arm 312. During this initial part of the movement of the bending member 302, the guide pin 322 moves along the linear rear portion 228 of the guide track 226, so that the bending member 302 cannot rotate about the bending axis B.

Linear movement of the bending member 302 continues until the guide pin 322 reaches the end of the rear portion 228 of the guide track 226. At this point, the guide pin 322 can move into the circumferentially-extending front portion 230 of the guide track 226. The bending member 302 is now able to turn about the bending axis B under the torsional force applied by the needle bending spring 308.

The turning movement of the bending member 302 causes the bending arm 312 to apply a bending force to the needle 16. The bending force causes the needle 16 to bend against the cylindrical former 310. In this way, the needle 16 conforms to the shape of a part-cylindrical section of the surface of the former 310, creating a smooth bend in the needle 16 that does not substantially restrict fluid flow through the needle.

FIGS. 6 and 7 show the device 100 after the deshielder sleeve 150 has been removed and when movement of the bending member 302 with respect to the carriage body 202 is complete. The needle 16 has been bent around the former 310 through an angle of approximately 90 degrees, so that the free end of the needle 16 now extends in an insertion direction H that is perpendicular to the container axis A.

The radius of curvature of the needle 16 after operation of the bending mechanism 300 is determined by the radius of the former 310, and the angle through which the needle 16 is bent is determined by the angle through which the bending member 302 turns. It will be appreciated that the needle 16 will tend to bend through a slightly smaller angle than the turning angle of the bending member 302 as a result of component clearances, manufacturing tolerances and elastic deformation of the components. Accordingly, in the illustrated example, the forward portion 230 of the guide track 226 (see FIG. 5(b), not shown in FIG. 6) is dimensioned so that the bending member 302 turns through an angle of approximately 95 degrees in total, which results in the needle 16 bending through an angle of approximately 90 degrees.

After the needle 16 has been automatically aligned with the insertion direction H upon removal of the deshielder sleeve 150, the operating sequence of the device continues when the user applies the contact face 112 of the device 100 to the injection site. As will now be described, the device 100 includes an insertion mechanism that is operable to apply an insertion force to the carriage assembly 200 to move the carriage assembly 200 in the insertion direction H with respect to the chassis 106 from a starting position, in which the needle 16 is shrouded, to an insertion position, in which the needle 16 extends through an aperture 116 disposed in the baseplate 111 of the chassis 106. The device 100 also includes a safety interlock mechanism that prevents accidental operation of the insertion mechanism.

Referring again to FIG. 4, the insertion mechanism includes an insertion spring 70. The insertion spring 70 comprises a tension spring that is arranged vertically in the housing 102 and attached between the carriage assembly 200 and the lower housing part 106. The insertion spring 70 has a lower hooked end termination that engages with a spring hook 118 formed on the top side of the baseplate 111 of the chassis 106 (see also FIG. 6).

The insertion spring 70 extends through the carriage body 202, so that an upper hooked end termination 74 of the insertion spring 70 is disposed on the upper side of the carriage body 202. As shown in FIG. 3, a spring tube 240 is provided in the lower carriage body part 206 and a circular aperture 242 is provided in the cover 104 to allow the insertion spring 70 to pass through the carriage body 202.

As shown in FIG. 4, the upper end termination 74 of the insertion spring 70 is attached to a pin part 502 of a spring coupling member 504. As will be explained in more detail below, the spring coupling member 504 forms part of a retraction mechanism of the device, and is mounted on the top side of the upper carriage body part 204. In this way, the insertion spring 70 acts to bias the carriage assembly 200 in the insertion direction H.

Movement of the cover 104, and hence also the carriage assembly 200, in the insertion direction H is initially prevented by the blocking member 126 of the trigger lever 120, which blocks movement of the stop 130 of the cover 104 along the channel 128 in the chassis 106, as explained above with reference to FIGS. 1 and 2. Thus the carriage assembly 200 is held in its starting position with respect to the chassis 106.

The interlock mechanism 170, which is arranged to prevent operation of the trigger lever 120 until the device 100 has been correctly positioned against an injection site, will now be described with reference to FIGS. 8 and 9.

The interlock mechanism 170 is mounted on the upper side of the baseplate 111 of the chassis 106. Referring first to FIG. 8(a), in which many parts have been omitted for clarity, the interlock mechanism 170 comprises a sensor element or sensor collar 172 that is received in the aperture 116 of the chassis 106. The sensor collar 172 is annular to define a central opening 174, to allow the needle 16 (not shown in FIG. 8) to pass through the sensor collar 172 upon insertion. The sensor collar 172 has an enlarged-diameter rim 176 on its upper side to retain the sensor collar 172 in the housing 102. A lower part of the sensor collar 172 is dimensioned to fit through the aperture 116, as can also be seen in FIG. 9(a).

A leg 192 extends upwardly from one side of the sensor collar 172. Referring additionally to FIG. 2, the leg 192 is dimensioned so that the leg 192 cooperates with the deshielder sleeve 150 when the deshielder sleeve 150 is still in place.

Referring again to FIG. 8(a), the sensor collar 172 is coupled to a beam element 178. The beam element 178 is angled, with a first section 180 extending from the sensor collar 172 towards a pivot 182, and a second section 184 extending from the pivot 182 towards a free end 186 that is disposed next to the inner face of the button 124 of the trigger lever 120. The beam element 178 is attached to the sensor collar 172 by means of a pin (not shown) on the beam element 178 that engages with a corresponding hole (not shown) in the sensor collar 172. The beam element 178 is attached to the chassis 106 at the pivot 182, for example by a clip.

The beam element 178 is biased by a pair of flat springs 188 that extend between the wall 114 of the chassis 106 and respective guide blocks 190 provided on the upper side of the baseplate 111 of the chassis 106. One end of each flat spring 188 is connected to the free end 186 of the beam element, and the opposite end of each flat spring 188 bears against the upper side of the baseplate 111 of the chassis 106, urging the free end 186 of the beam element in the upward direction and the sensor collar 172 in the downward direction.

In this way, the interlock mechanism 170 is biased into a first state, shown in FIGS. 8(a) and 9(a), in which the sensor collar 172 projects from the contact face 112 (i.e. the bottom face of the sensor collar 172 stands proud of the contact face 112) and the free end 186 of the beam element 178 is positioned to block inward movement of the trigger button 124. In this first state, therefore, the interlock mechanism 170 prevents unintentional operation of the trigger button 124, with the free end 186 of the beam element 178 acting as a trigger blocking element.

In the starting state of the device 100, when the deshielder sleeve 150 is still in place as shown in FIG. 2, upward movement of the sensor collar 172 is prevented by abutment of the leg 192 against the deshielder sleeve 150. Accordingly, the interlock mechanism 170 cannot be switched out of the first state until the deshielder sleeve 150 has been removed and the needle bending mechanism 300 has bent the needle 16 into alignment with the insertion direction H.

Figure 8:
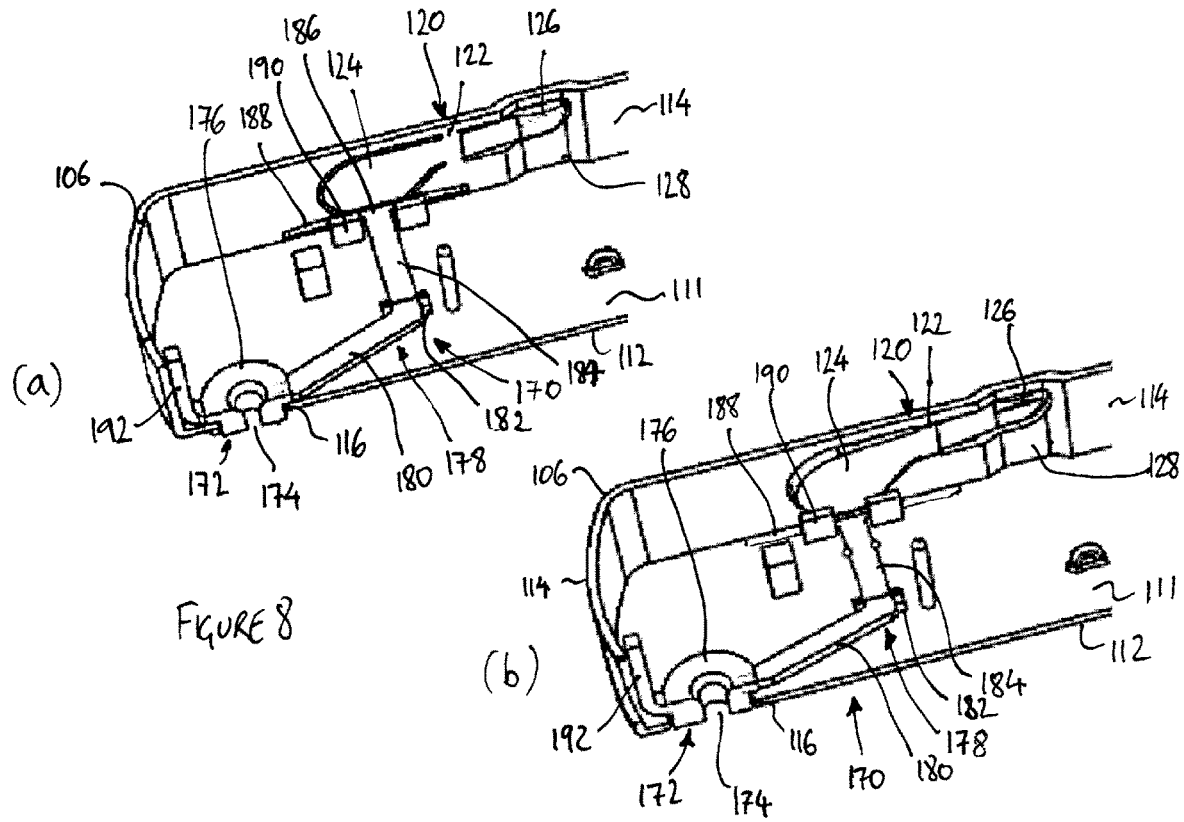
Figure 9:
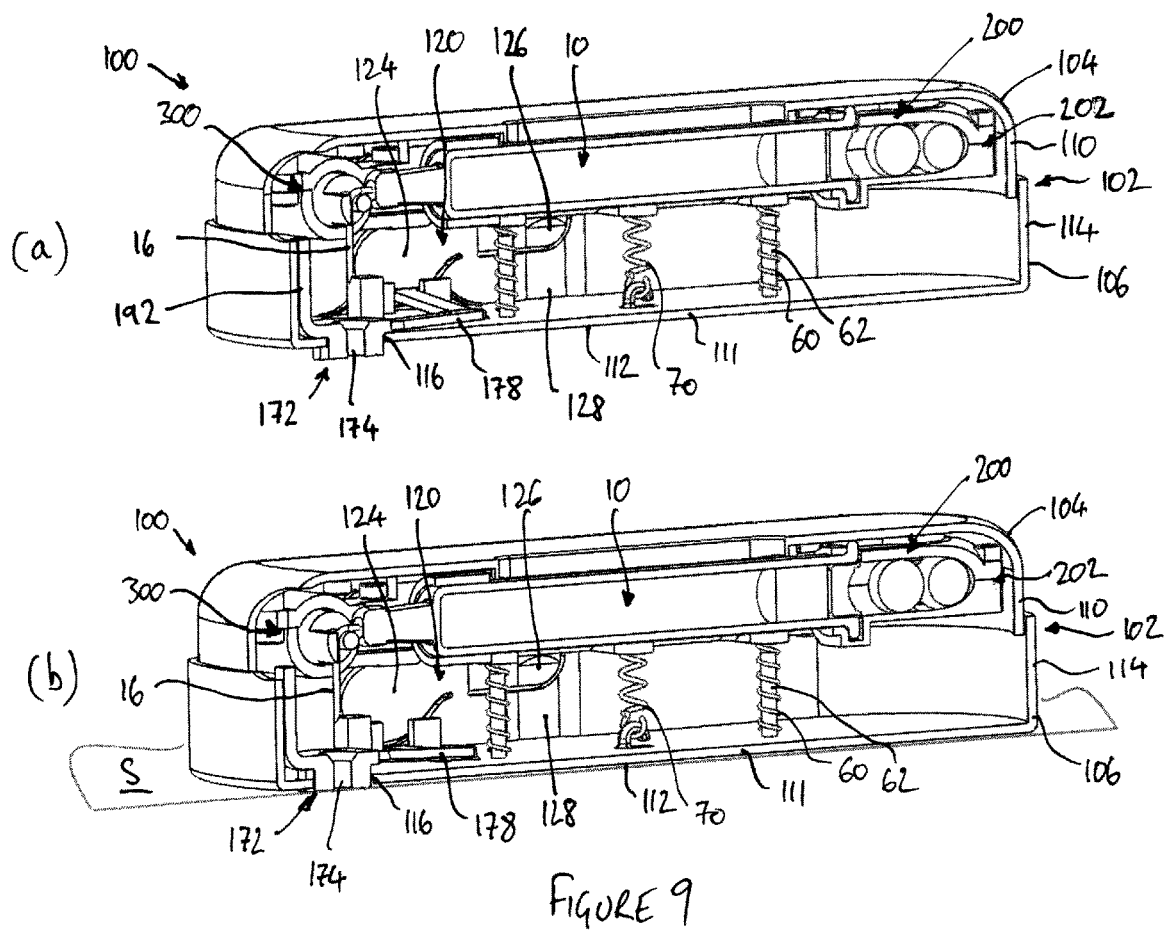

When the deshielder sleeve 150 has been removed, as shown in FIG. 9(a), upward movement of the leg 192 is no longer encumbered and the sensor collar 172 can now move in an upward direction (i.e. opposite to the insertion direction H) with respect to the chassis 106, into a retracted position. Thus, when the device 100 is positioned with the contact face 112 pressed against an injection site S, as shown in FIG. 9(*b*), the sensor collar 172 is displaced upwardly, and the beam element 178 turns about the pivot 182 so that the free end 186 of the beam element 178 moves downwards, against the bias of the flat springs 188. In this way, the interlock mechanism 170 can be switched into a second state, shown in FIGS. 8(*b*) and 9(*b*), in which the free end 186 of the beam element 178 no longer blocks inward movement of the trigger button 124. The sensor collar 172 thus acts as a sensor that responds to detection of the skin at the injection site S by switching the interlock mechanism 170 from the first state to the second state. It will be appreciated that the sensor collar 172 may not retract fully into the chassis 106 when in the retracted position, and that the bottom face of the sensor collar 172 may instead still be slightly proud of the contact face 112. However, a substantial majority of the contacting area between the device 100 and the injection site is through the contact face 112 itself.

If the device 100 is now removed from the injection site S before the trigger button 124 has been pressed, the flat springs 188 cause the interlock mechanism 170 to return to the first state, to block operation of the trigger button 124 once more.

Figure 10:
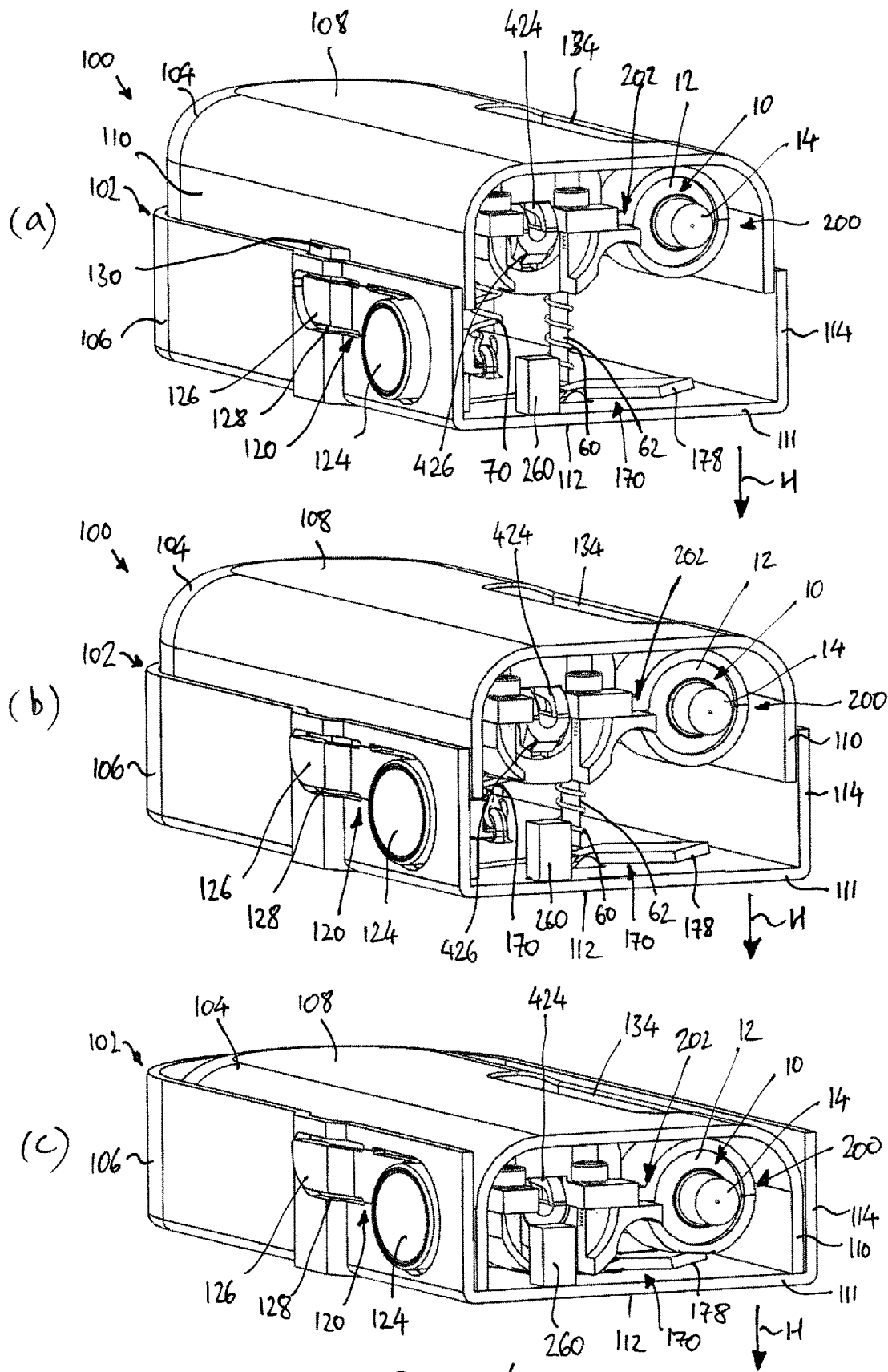

FIG. 10(*a*) shows another view of the device 100 when the contact face 112 has been pressed against an injection site, so that the interlock mechanism 170 is held in the second state. Only the beam element 178 of the interlock mechanism 170 can be seen in FIG. 10(*a*). In FIG. 10(*a*), the trigger lever 120 is still in its neutral position, with the blocking member 126 preventing movement of the stop 130 down the channel 128.

If the trigger button 124 is now pressed inwardly, the trigger lever 120 pivots away from the neutral position to move the blocking member 126 out of the channel 128 (see also FIG. 8(*b*)). The stop 130 of the cover 104 can now move down the channel 128 to start an insertion stroke of the carriage assembly 200. The cover 104, together with the carriage assembly 200, thus moves with respect to the chassis 106 and in the insertion direction H under the tension of the insertion spring 70. FIG. 10(*b*) shows the device 100 in an intermediate state during the insertion stroke of the carriage assembly 200.

Movement of the cover 104 and the carriage assembly 200 continues until the bottom edge of the skirt 110 of the cover 104 comes into contact with the baseplate 111 of the chassis 106, as shown in FIG. 10(*c*).

FIGS. 11 and 12 show further views of the device 100 at the end of the insertion stroke. FIG. 11 illustrates the low-profile configuration of the device, with the cover 104 now telescoped fully into the chassis 106. The chassis 106 does not move during the insertion stroke, so that the contact face 112 of the device 100 remains stationary with respect to the injection site.

As shown in FIG. 12, movement of the carriage assembly 200 in the insertion direction H causes the bent needle 16 to extend out of the aperture 116 in the baseplate 111 of the chassis 106, passing through the opening 174 in the sensor collar 172. In this way, the needle 16 protrudes from the contact face 112 of the device 100 to pierce the skin at the injection site.

Delivery of the medicament 20 through the needle is performed by operation of the drive mechanism 400 of the device 100, as will now be described with reference to FIGS. 3 and 4, and also with reference to FIG. 13(*a*), which shows the device 100 at an intermediate position during the insertion stroke, before activation of the drive mechanism 400, such that the drive mechanism 400 is in an initial, unfired state.

The drive mechanism 400 includes a drive means in the form of a drive spring 40 that is arranged alongside the syringe 10 and along a drive axis D that is parallel to the container axis A. The drive spring 40 is housed in a generally cylindrical cavity 208 in the carriage body 202.

The drive mechanism 400 further includes a guide tube 402, a piston member 404 that is slidably received in the guide tube 402, and a force transmission means comprising a plurality of balls 406 arranged in a linear array along a J-shaped guide track 408 (see FIGS. 3 and 4).

The guide track 408 is defined in part by the upper and lower carriage body parts 204, 206 and in part by the guide tube 402. The guide tube 402 is received in the cylindrical cavity 208 of the carriage body 200, inside the drive spring 40. The guide tube 402 accommodates several of the balls 406 and defines a long linear portion of the guide track 408. As best shown in FIG. 3, the carriage body parts 204, 206 are shaped to define a U-shaped part 410 of the guide track 408 that extends from the cylindrical cavity 208 and around a sprocket 550, and opens into the bore of the syringe barrel 12. The balls 406 are sized to fit within the bore of the syringe barrel 12.

As can be seen most clearly in FIG. 13(*a*), the piston member 404 is received in the end of the guide tube 402 closest to the needle bending mechanism 300. The piston member 404 comprises an end face 412 that is cup-shaped for cooperation with the closest one of the balls 406. A rib 414 (see FIG. 3) is provided on the upper side of the piston member 404. The guide tube 402 includes a slit 416 that extends parallel to the drive axis D to receive the rib 414, so that the piston member 404 can slide within the guide tube 402 without rotating about the axis of the guide tube 402.

The piston member 404 is biased along the drive axis D and away from the needle bending mechanism 300 by the drive spring 40. The drive spring 40 comprises a helical tension spring with hooked end terminations and is accommodated concentrically around the linear portion of the guide track 408, in the space between the guide tube 404 and the cylindrical cavity 208 in the carriage body 202. In this way, the guide tube 404 also acts as a spring guide for the drive spring 40. One end termination 42 of the drive spring 40 is hooked into an aperture 252 in the upper carriage body 204 (see FIG. 3). Referring back to FIG. 13(*a*), the opposite end termination 44 of the drive spring 40 passes through a slot 420 in the upper side of the piston member 404 to locate in a frustoconical bore 422 of the piston member 404. In the initial state of the drive mechanism 400, the drive spring 40 is stretched along its length to store energy and, as will be described in more detail below, is arranged to apply a linear force to the piston member 404 along the drive axis D when the drive mechanism 400 is operated.

Referring still to FIG. 13(*a*), the piston member 404 is provided with a pair of spring fingers 424 disposed on either side of the slot 420 on the rear side of the piston member 404, and a latch formation 426 that extends along the front side of the piston member 404. The spring fingers 424 and the latch formation 426 can also be seen in FIG. 10.

With the drive mechanism 400 in its initial state, as shown in FIG. 13(*a*), the latch formation 426 extends through an aperture 254 in the carriage body 202 (see also FIG. 3, in which the position of the aperture 254 in the lower carriage body part 206 can be seen). The latch formation 426 has a hook-shaped head arranged to releasably engage with a stop 256 formed on the lower carriage body part 206 at the side of the aperture 254. At the same time, the spring fingers 424 press against the upper side of the aperture 254 to keep the latch formation 426 in engagement with the stop 256 on the lower carriage body 206. Thus the latch formation 426 prevents linear movement of the piston member 404 under the influence of the drive spring 40 when the head of the latch formation 426 is engaged with the lower carriage body 406.

A firing block 260 is provided on the baseplate 111 of the chassis 104. As will be explained in more detail below, the firing block 260 is positioned to cooperate with the latch formation 426 to release the piston member 404 for movement along the drive axis D in a delivery stroke during the operating sequence of the device 100.

Referring to FIG. 12, a shock absorber cup 430 is received in the barrel 12 of the syringe 10, between the stopper 22 and the array of balls 406. One face 432 of the shock absorber cup 430 is shaped to cooperate with the closest one of the balls 406. The shock absorber cup 430 is of a plastics foam material, for example a polyurethane foam, to cushion the impact between the balls 406 and the stopper 22 upon activation of the drive mechanism 400.

The balls 406 are arranged along the guide track 408 to form a chain or array. The periphery of the sprocket 550 is shaped to cooperate with the balls 406 in the adjacent track 408, so that movement of the balls 406 along the guide track 408 turns the sprocket 550. The sprocket forms part of a retraction mechanism of the device, which will be explained in more detail below.

In the illustrated device 100, the ball 406 at the end of the array closest to the piston member 404 is spaced from the face 412 of the piston member 404, and the ball 406 at the other end of the array is spaced from the face 432 of the shock absorber cup 430. It will however be appreciated that the balls 406 are not attached to one another and that the spacing of the balls 406 may differ in practice. In preferred arrangements, smaller clearances than those shown are present between the respective contact faces 412, 432 and the corresponding balls 406. It is also possible for the contact faces 412, 432 to be in contact with the corresponding balls 406, in which case the shock absorber cup 430 can deform to take up any difference in length between the array of balls 406 and the distance between the faces 412, 432 when the components are in their initial positions.

The drive mechanism 400 is automatically triggered during movement of the carriage assembly 200 towards the contact face 112 of the device 100. Towards the end of the insertion stroke of the carriage assembly 200, the carriage assembly 200 reaches an activation position in which the firing block 260 on the chassis 106 comes into contact with the head of the latch formation 426 on the piston member 404 (see FIG. 13(a)). The firing block 260 displaces the latch formation 426 towards the top face 108 of the device 100, bending the spring fingers 424 and causing the latch formation 426 to disengage from the stop 256 on the lower carriage body part 206, as shown in FIG. 13(b).

In this way, the drive mechanism 400 of the device 100 is activated, and linear movement of the piston member 404 within the guide tube 402 under the load of the drive spring 40 can now take place. As the piston member 404 moves along the guide tube 402 in a delivery stroke, the piston member 404 pushes the balls 406 around the guide track 408 and into the syringe barrel 12. The load of the drive spring is thus transferred through the array of balls 406 to the ball 406 closest to the shock absorber cup 430. In turn, the shock absorber cup 430 pushes the stopper 22 of the syringe 10 distally to expel medicament through the needle 16. The shock absorber cup 430 reduces the risk of impact damage to the syringe 10 and reduces the impact sound.

Linear movement of the piston member 404 continues until the rib 414 on the piston member 404 reaches the end of the slit 416 in the guide tube 402. At this point, distal movement of the stopper 22 of the syringe 10 ceases and the delivery stroke ends.

After delivery of the medicament, a retraction mechanism of the device 100 operates to retract the needle 16 from the injection site. The components and operation of the retraction mechanism will now be described.

FIG. 14 shows the device 100 sectioned through a vertical plane of the device that is parallel to and mid-way between the container axis A and the drive axis D. A pair of retraction springs 60 are provided to bias the carriage assembly 200 away from the contact face 112 of the device 100, in a direction opposite to the insertion direction H. In this example, each retraction spring 60 is a helical compression spring, and is mounted on a corresponding guide pin 62 that extends upwardly from the baseplate 111 of the chassis 106. As shown additionally in FIG. 3, the carriage body 202 includes a pair of tubular guides 261 for receiving the retraction springs 60 and the corresponding guide pins 62. Each guide 261 has an inwardly-directed flange 262 at its upper end to provide a seat for the respective retraction spring 60.

The combined force applied to the carriage assembly 200 by the retraction springs 60 is less than the force applied to the carriage assembly 200 by the insertion spring 70, so that the force of the insertion spring 70 overcomes the force of the retraction springs 60 during the insertion stroke of the carriage assembly 200. Thus the retraction springs 60 are compressed between the carriage body 202 and the baseplate 111 of the chassis 106 during the insertion stroke.

As described above, the insertion spring 70 is coupled to the carriage body 202 by way of a spring coupling member 504 having a pin part 502, with the upper end termination 74 of the insertion spring 70 hooked over the pin part 502. The coupling member 504 is slidable with respect to the carriage body 202. In this way, during operation of the retraction mechanism, the pin part 502 of the coupling member 504 can be withdrawn from engagement with the insertion spring 70 to decouple the insertion spring 70 from the carriage assembly 200.

The coupling member 504 is mounted on the upper side of the upper carriage body part 204 and is guided for linear movement thereon by a channel 270, visible only in FIG. 3. A lower part of the coupling member 504 extends into the channel 270, and the coupling member 504 is secured in the channel 270 by attachment of the lower part of the coupling member 504 to a bracket 506. The bracket 506, in turn, is in sliding engagement with a guide rod 272 that is formed on the spring tube 240 on the lower carriage body part 206. Both the channel 270 and the guide rod 272 extend parallel to the container axis A and the drive axis D.

A decoupling spring 80, in the form of a helical compression spring, is disposed concentrically around the guide rod 272. The decoupling spring 80 bears against the bracket 506 at one end and against the spring tube 240 at its opposite end, so that the coupling member 504 is biased for linear movement in a direction away from the needle bending mechanism 300.

Before activation of the retraction mechanism, movement of the coupling member 504 is prevented by a release lever 520. Referring to FIGS. 15(a) and 15(b), which are crosssections on two horizontal planes, and also to FIG. 3, the release lever 520 comprises a ring-shaped hub 522, a blocking finger 524 that extends away from the hub 522 towards the coupling member 504, and a release arm 526 that extends away from the hub 522 generally in the opposite direction to the blocking finger 524. A flat spring 528 is also provided, which extends from the hub 522 alongside the release arm 526.

Referring additionally to FIG. 16, the release lever 520 is mounted on the upper carriage body part 204, with the hub 522 fitted over the top end of one of the tubular retraction spring guides 261. The flat spring 528 bears against a vertical surface 264 of the upper carriage body part 204.

The flat spring 528 biases the release lever 520 so that the release arm 526 contacts a stop formation 276 (not shown in FIG. 16) on the upper carriage body part 204. As shown most clearly in FIG. 15(a), when the release lever 520 is in this position, the blocking finger 524 abuts the coupling member 504, resisting movement of the coupling member 504 under the influence of the decoupling spring 80.

The sprocket 550, which is driven to rotate by the balls 406 during medicament delivery, is provided on its upper side with a pinion gear 552. The pinion gear 552 extends through an aperture 278 in the upper carriage body part 204 (see FIG. 3). The pinion gear 552 drives a wheel in the form of an annular gear 554 that is retained by a part-circular guide wall 280 on the upper carriage body part 204. The outer edge of the annular gear 554 is formed with an annular groove 556 to accept a reduced-thickness tip 558 of the release arm 526 of the release lever 520. As can be seen most clearly in FIG. 15(a), the groove 556 of the annular gear 554 is interrupted at one position by a tab 560.

The tab 560 is initially disposed to the left of the tip 558 of the release arm 526 (as viewed in FIG. 15(a)). Upon operation of the drive mechanism 400, the sprocket 550 and the pinion 552 are driven to rotate in a clockwise direction. The pinion 552 drives the annular gear 554 (with, in this example, a 1.5:1 reduction in gear ratio), which likewise rotates in a clockwise direction. This move the tab 560 clockwise. By virtue of the gear train formed by the pinion 552 and the annular gear 554, the annular gear 554 rotates through a smaller angle than the sprocket 550. In the illustrated example, the sprocket 550 rotates through approximately 1.5 turns during operation of the drive mechanism 400, and this causes approximately one full turn of the annular gear 554.

Towards the end of medicament delivery, the tab 560 engages with the tip 558 of the release arm 526 of the release lever 520. This causes the release lever 520 to pivot in an anticlockwise direction, moving the blocking finger 524 out of engagement with the coupling member 504. Thus the coupling member 504 is released for movement under the bias of the decoupling spring 80.

A rotary damper 570 is provided to control the speed of movement of the coupling member 504. The rotary damper 570 is mounted on the upper side of the coupling member 504, and comprises a toothed rotary element or cap 572 that is engaged with a rack 282 formed on the upper carriage body part 204. The cap 572 encloses a chamber (not shown) that contains a viscous fluid, such as silicone grease. As the coupling member 504 moves linearly with respect to the carriage body 202, the cap 572 is driven to rotate by the rack 282, and is arranged to move an internal vane 283 (see FIG. 15(a)) through the viscous fluid in the chamber, which resists movement of the cap 572 and hence retards the speed of the coupling member 504.

Operation of the retraction mechanism will now be described with reference to FIG. 17.

FIG. 17(a) shows the device 100 mid-way through medicament delivery, when the plunger 22 has been driven partially down the body 12 of the syringe 10. The coupling member 504 is still held in its initial position by the release lever 520, and the retraction spring 70 (only the upper end termination 74 of which can be seen in FIG. 17(a)) is still hooked over the pin part 502 of the coupling member 504. The sprocket 550 has been rotated by the balls 406 of the drive mechanism and the pinion 552 has driven the annular gear 554 to move the tab 560 clockwise from its initial position.

FIG. 17(b) shows the device 100 during a later stage of medicament delivery, in which further rotation of the sprocket 550 has resulted in further rotation of the annular gear 554, bringing the tab 560 closer to the tip 558 of the release arm 526 of the release lever 520.

FIG. 17(c) shows the device 100 at a still later stage of medicament delivery. At this point, further rotation of the annular gear 554 has brought the tab 560 into contact with the tip 558 of the release arm 526, and the tab 560 has displaced the release arm 526 against the bias of the flat spring 528 to activate the retraction mechanism. Now, the blocking finger 524 no longer blocks movement of the coupling member 504. At this stage, the coupling member 504 begins to move towards the sprocket 550 under the bias of the decoupling spring 80.

The blocking finger 524 moves clear of the coupling member 504 before the movement of the piston member 404 (not shown in FIG. 17) ends. In this way, it is ensured that the coupling member 504 will always be released for linear movement before the delivery stroke ends, even accounting for manufacturing tolerances and the like. In one example, the blocking finger 524 moves clear of the coupling member 504 when the piston member 404 is approximately 1 mm from the end of its travel.

Operation now continues with simultaneous movement of both the piston member 404, and hence the stopper 22 of the syringe 10, and the coupling member 504. As shown in FIG. 17(d), as the coupling member 504 moves towards the sprocket 550, the pin part 502 of the coupling member 504 progressively slides under from the upper end termination 74 of the insertion spring 70, with the insertion spring 70 being held in place by the spring tube 240 (not visible in FIG. 17). The damper 570 acts to restrict the speed of movement of the coupling member 504 as the cap 572 of the damper 570 travels along the rack 282.

Figure 17:
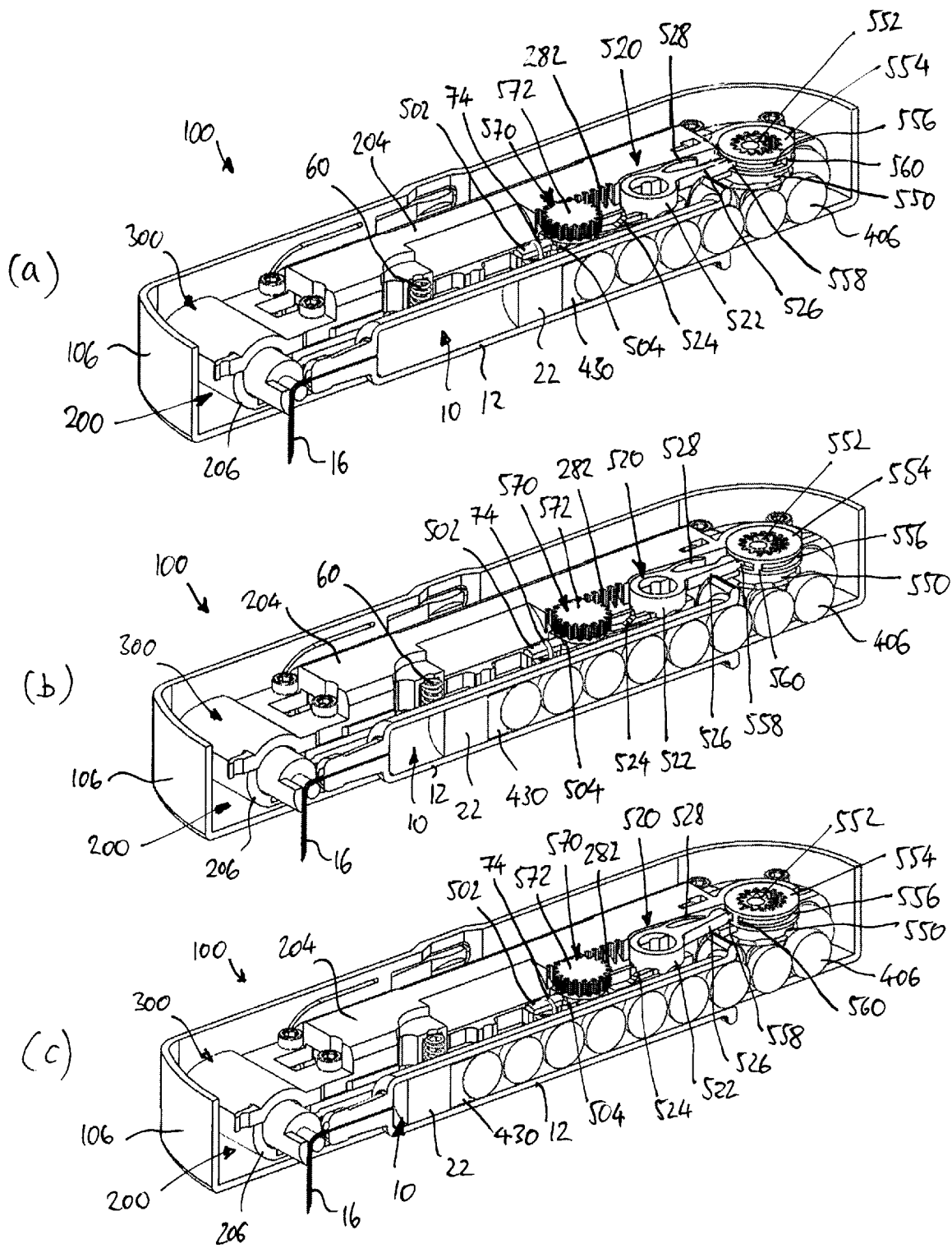
Figure 17:
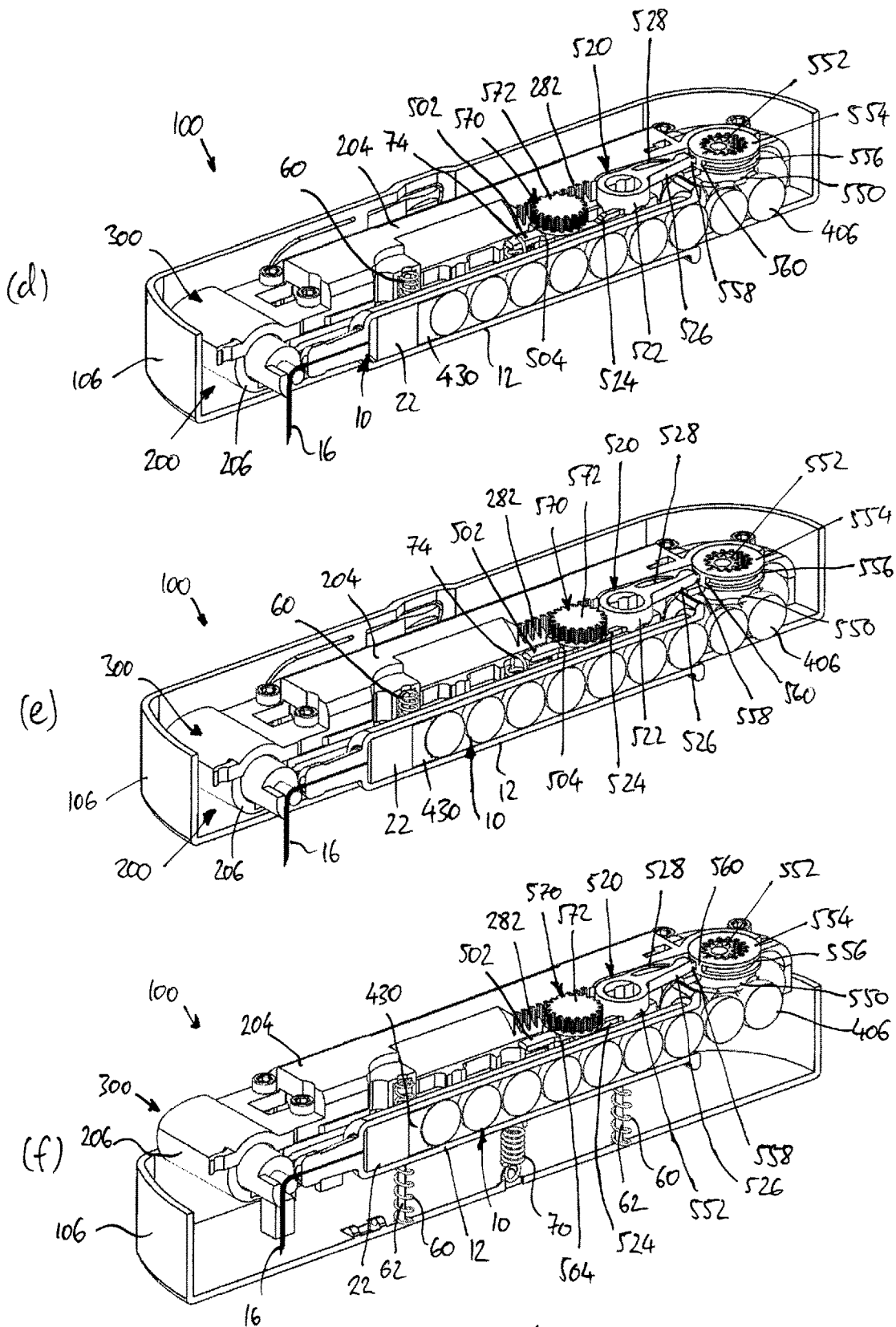

Eventually, the pin part 502 of the coupling member 504 is withdrawn from the upper end termination 74 of the insertion spring 70, as shown in FIG. 17(e), to decouple the insertion spring 70 from the carriage assembly 200. The insertion spring 70 no longer applies a force to the carriage assembly 200, so that the carriage assembly 200 moves upwardly, opposite to the insertion direction H, under the force applied by the retraction springs 60. The upward movement of the carriage assembly 200 causes withdrawal of the needle 16 from the injection site, as shown in FIG. 17(f). The cover 104 (not shown in FIG. 17) "pops up" with the carriage assembly 200 to provide a visual and tactile indication to the user that medicament delivery has been completed and that the device 100 can be removed from the injection site. The cover 104 is retained by suitable stop features (not shown), disposed for example on the periphery of the cover 104 and the chassis 106. The needle 16 is now safely retracted within the housing 102, and the device 100 can be disposed of.

The provision of the damper 570 creates a time delay between activation of the retraction mechanism (i.e. displacement of the release arm 526 by the tab 560) and the decoupling of the insertion spring 70 to retract the needle 16. This time delay ensures complete delivery of the medicament, by allowing the delivery stroke to end and allowing the needle 16 remain in place in the injection site for a short period after end of the delivery stroke before retraction of the needle 16. In one example, a time of 3 to 4 seconds elapses between the blocking finger 524 moving clear of the coupling member 504 and the pin part 502 of the coupling member 504 decoupling from the insertion spring 70, although a longer or shorter delay could be provided if desired.

From the above, it will be understood that the retraction springs 60, the sprocket 550 and gears 552, 554, the releasable coupling arrangement formed by the release lever 520 and the coupling member 504 and the decoupling spring 80 together form a retraction mechanism for the device 100 that, after activation, moves the carriage assembly 200 in a retraction direction opposite to the insertion direction H. Furthermore, the rotary damper 570 defined by the cap 572 and the rack 282 provide a time delay mechanism that creates a delay time between activation of the retraction mechanism, and the start of movement of the carriage assembly 200 in the retraction direction.

From the above description, it will be appreciated that the components of the device are selected and arranged to provide a device with a low-profile form factor. Thus the device can be comfortably gripped and held stationary against an injection site by a user, held in place with a suitable strap or holder, affixed to the injection site with adhesive tape, or adhered to the injection site with an adhesive applied to the contact face 112 of the device 100. The relatively large surface area of the contact face 112 of the device 100 means that the device 100 can be held firmly against the injection site with minimal discomfort and marking, since the holding force is spread over a large area. In this way, the device is particularly suitable for the delivery of relatively large volumes of medicament over a relatively long period of time. Furthermore, impact loads that may occur upon insertion of the needle, in particular at the end of the insertion stroke when the cover 104 contacts the chassis 106 are dissipated over the large area provided by the contact face 112, minimising the impression of such loads on the user.

To reduce further such impact loads, cushioning elements may be provided to act as shock absorbers between impacting components. For example, cushioning elements may be provided on the lower edge of the skirt 110 of the cover 104 or at the periphery of the baseplate 111 of the chassis 106.

Alternatively, or in addition, cushioning elements may be provided between the retraction spring guide pins 62 and the flanges 262 of the corresponding guides 260. The cushioning elements may be formed from an elastomeric foam material, such as a polyurethane foam.

Several further modifications and variations of the device of FIGS. 1 to 17 are possible. It will be appreciated, for example, that the device described with reference to FIGS. 1 to 17 includes several mechanisms that could be used independently or in different combinations in other devices, and that one or more of the mechanisms could be substituted with alternative arrangements or omitted as appropriate for a particular application.

In the illustrated embodiment, a single needle bending spring that acts in both compression and torsion is used to drive movement of the bending member of the needle bending mechanism. In alternative arrangements, two springs can be provided for this purpose. For example, a compression spring can be used to drive axial movement of the bending member along the bending axis, and a torsion spring can be used to drive turning movement of the bending member about the bending axis. Alternatively, or in addition, the guide track can be shaped to provide a cam action to assist or drive turning movement of the bending member.

Many further alternative mechanisms for driving and guiding movement of the bending member in the needle bending mechanism are possible. For example, the needle drive spring could be a tension spring. Instead of one or more helical drive springs, other spring types or alternative energy storage means could be used. Part or all of the movement of the bending member could be manually driven, for example by direct manipulation of a shaft part of the bending member, or indirectly through a suitable mechanism.

In the illustrated examples, operation of the bending mechanism is activated by removal of a user-removable component in the form of a deshielder shield. In some cases, the user-removable component could instead be a safety tab or a packaging part. In other examples, a retaining means such as a releasable or removable clip may be provided to hold the bending mechanism in its initial state. In this case, operation of the bending mechanism could be triggered by a specific action, such as operation of a button or slider, on the part of the user. It is also conceivable that axial movement of the bending member could be triggered automatically upon removal of the deshielder to engage the bending member with the needle, whilst the turning movement to bend the needle could be triggered separately.

The bending mechanism can be arranged to produce substantially any desired cannula or needle shape and angle through appropriate design of the needle engagement formation of the bending member and the guide track and other parameters, such as the orientation of the bending axis with respect to the container axis. It is also conceivable that the cannula could be pre-bent or otherwise arranged for alignment with the insertion direction, in which case the bending mechanism could be omitted from the device.

In the illustrated embodiment, the carriage assembly moves in the downward direction with respect to the contact surface to insert the needle and in the upward direction to withdraw the needle. However, other arrangements are possible, and it is conceivable that the insertion direction may be at a non-perpendicular angle to the container axis. In such cases, the needle would be bent through a corresponding non-perpendicular angle. For instance, it would be possible to insert the needle at an inclined angle with respect to the contact face of the device.

Many variations of and alternatives to the illustrated trigger arrangement are possible. In general, any suitable arrangement that first holds the carriage assembly in the starting position and then releases the carriage assembly for movement in the insertion direction could be used. Whilst in the illustrated example, the trigger arrangement acts against the cover, the trigger arrangement could instead act against the carriage body or another part of the carriage assembly. The trigger arrangement could be mounted on the top face of the device or on one of the end sides of the device. A lever, button, slider, knob or any other suitable trigger component could be used to operate the trigger arrangement. More than one trigger component could be provided. For example, trigger components could be provided on each side of the device, and release of the carriage assembly could be achieved by manipulation of either one of the trigger components (for example to allow left- or right-handed use), or upon simultaneous manipulation of both trigger components (to provide additional security against accidental operation of the device).

In the illustrated example, the interlock mechanism acts directly to block movement of the trigger lever. However, other suitable interlock mechanisms can be contemplated that would allow movement of the trigger lever but otherwise prevent movement of the carriage assembly from the starting position. It is also conceivable that the interlock mechanism could be omitted.

Alternative drive mechanisms for driving the stopper of the syringe could be employed. For example, the drive spring need not be arranged concentrically around a part of the array of balls. Instead, the drive member could be driven by one or more tension springs arranged alongside a part of the array of balls. Instead of a tension spring, the drive member could be driven by a compression spring, constant force spring, power spring or any other suitable means for applying a force.

Any suitable releasable latch or retaining arrangement may be used to hold the piston member in its initial position and to release the piston member for movement along the drive axis. For example, in an alternative to the illustrated latch arrangement, the piston member may be retained by a retaining pin or other retaining means that moves out of engagement with the piston member when the carriage assembly moves in the insertion direction to activate the drive mechanism and transfer the force of the spring to the balls to drive the stopper of the syringe. Other drive arrangements that do not use a piston member are also possible. For example, it is conceivable that the sprocket could be driven by a driving element, such as a power spring, to apply a drive force to the balls or other force transmission means.

In the illustrated embodiment, an array of balls is provided to transmit force from the piston member to the stopper of the syringe. Preferably, the balls are metal ball bearings, which allow transmission of the force with minimal flexing or elastic deformation. However, it is conceivable that other force transmission means could be provided. For example, a flexible plastic rod, a close-wound spring, a link chain or any other suitable arrangement could be used. It is also possible that the force transmission means could be integral with or fixed to the piston member.

Furthermore, in the illustrated example, the drive axis along which the piston member moves is parallel to and spaced from the axis of the container, along which the stopper moves to expel the medicament. The piston member is disposed alongside the container, and the piston member and the stopper move in opposite directions relative to the carriage body. Thus, the force transmission means serves to redirect the force of the drive spring through 180 degrees. This results in a relatively compact arrangement. However, other arrangements of the components within the carriage are possible, including those in which the drive axis and the container axis are non-parallel, or in which the drive axis and the container axis are coaxial.

The use of a rotary damper provides a compact and predicable means for introducing a delay time between activation of the retraction mechanism and the retraction movement of the needle. Preferably, the damping fluid is selected such that the viscosity of the damping fluid is not substantially changed over the range of temperatures in which the device might be expected to be used, which may include use straight after removal of the device from a refrigerator and/or use of the device in relatively hot environmental conditions.

Other time delay mechanisms could be used. For example, instead of a rotary damper, a linear viscous damper or other damping arrangement could be used. It is also conceivable that an escapement mechanism, gear train or other mechanical delay arrangement could be used. It will also be appreciated that, in some applications, a time delay mechanism may not be required, in which case the insertion spring could be decoupled from the carriage arrangement substantially immediately upon activation of the retraction mechanism.

In some further applications, the retraction mechanism could be omitted, and the needle could be withdrawn manually after delivery of the medicament.

An outer casing may be provided over the cover, so that the dimensions of the device do not change in use. Such an outer casing may be transparent or include a window to allow movement of the cover to be seen by the user during operation of the device.

The above-described examples show the device in use with a pre-filled syringe having a permanently attached needle, but the assembly could equally be used with other arrangements, such as a medicament container with a separate, attachable or connectable needle or cannula. To this end, in some arrangements, the container and/or the drive mechanism need not be retained by or moveable with the carriage.

Further modifications and variations of the examples described above are also possible without departing from the scope of the invention as defined in the appended claims.

The invention claimed is:

1. A medicament delivery device for delivery of medicament from a container into an injection site through a cannula, the device comprising:
   a chassis;
   a drive mechanism for driving a piston member of the container along a container axis (A) to expel the medicament through the cannula;
   a carriage for retaining the container, the cannula and the drive mechanism;
   an insertion mechanism for moving the carriage in an insertion direction (H) relative to the chassis from a starting position; and
   a cannula bending mechanism for bending the cannula about a bending axis (B) to substantially align at least an end part of the cannula with the insertion direction (H) prior to movement of the carriage in the insertion direction (H),
   wherein the bending mechanism comprises a bending member that is axially moveable along the bending axis (B) into engagement with the cannula and turnable about the bending axis (B) to apply a bending force to the cannula, and
   wherein a user-removable component blocks axial movement of the bending member until the user-removable component has been removed from the device for triggering operation of the bending mechanism.

2. The medicament delivery device according to claim 1, wherein the user-removable component comprises a deshielder for removing a shield from the cannula.

3. The medicament delivery device according to claim 1, comprising a contact face for contacting the injection site, and wherein the bending mechanism is arranged to align the cannula with an opening in the contact face upon movement of the carriage in the insertion direction (H).

4. The medicament delivery device according to claim 3, wherein the container axis (A) is substantially parallel to the contact face.

5. The medicament delivery device according to claim 3, wherein the bending axis (B) is substantially parallel to the contact face.

6. The medicament delivery device according to claim 1, wherein the bending axis (B) is substantially perpendicular to the container axis (A).

7. The medicament delivery device according to claim 1, further comprising an interlock arrangement for preventing operation of the insertion mechanism until the cannula has been aligned with the insertion direction (H).

8. The medicament delivery device according to claim 7, wherein the interlock arrangement is switchable from a first position in which operation of the insertion mechanism is prevented to a second position in which operation of the insertion mechanism is possible.

9. The medicament delivery device according to claim 8, wherein the interlock arrangement is held in the first position by the user-removable component, and wherein the interlock arrangement is switchable to the second position after removal of the user-removable component.

10. The medicament delivery device according to claim 8, comprising a sensor for switching the interlock arrangement to the second position when a contact face of the device is placed against the injection site.

11. The medicament delivery device according to claim 7, wherein the insertion mechanism comprises a latch arrangement for holding the carriage in the starting position, and a trigger component operable to release the latch arrangement to allow movement of the carriage in the insertion direction (H), and wherein operation of the trigger component is blocked by the interlock arrangement when the interlock arrangement is in a first position.

12. The medicament delivery device according to claim 1, wherein the drive mechanism comprises a drive member that is movable with respect to the carriage upon activation of the drive mechanism, a driver for applying a driving force to the drive member along a drive axis (D), and a force transmitter for transmitting the driving force from the drive member to the piston member, wherein the drive axis (D) is substantially parallel to and spaced from the container axis (A).

13. The medicament delivery device according to claim 12, wherein the driver is arranged around or alongside at least part of the force transmitter.

14. The medicament delivery device according to claim 13, wherein the driver comprises a tension spring arranged concentrically around at least part of the force transmitter.

15. The medicament delivery device according to claim 1, wherein the drive mechanism is activated in response to the carriage reaching an activation position during movement of the carriage in the insertion direction (H).

16. The medicament delivery device according to claim 15, comprising a drive trigger associated with the chassis for activating the drive mechanism when the carriage reaches the activation position.

17. The medicament delivery device according to claim 1, further comprising a retraction mechanism for moving the carriage with respect to the chassis in a retraction direction opposite to the insertion direction (H) to withdraw the cannula after the delivery of the medicament.

18. The medicament delivery device according to claim 17, wherein the insertion mechanism comprises an insertion spring for biasing the carriage in the insertion direction (H), and wherein the retraction mechanism comprises a coupling arrangement for releasably coupling the insertion spring to the carriage and for decoupling the insertion spring from the carriage upon activation of the retraction mechanism.

19. The medicament delivery device according to claim 18, wherein the drive mechanism is operable to move the piston member through a delivery stroke in the container, and wherein the retraction mechanism is activated by the drive mechanism before an end of the delivery stroke.

20. The medicament delivery device according to claim 19, arranged such that the insertion spring is decoupled from the carriage after a delay time has elapsed following the activation of the retraction mechanism.

21. The medicament delivery device according to claim 18, wherein the coupling arrangement comprises a coupling member that is moveable with respect to the carriage to decouple the insertion spring from the carriage and a retaining member arranged to prevent movement of the coupling member before the activation of the retraction member and to allow movement of the coupling member upon the activation of the retraction mechanism.

22. The medicament delivery device according to claim 21, arranged such that the insertion spring is decoupled from the carriage after a delay time has elapsed following the activation of the retraction mechanism; and
further comprising a damper for retarding the movement of the coupling member after the activation of the retraction mechanism.

23. The medicament delivery device according to claim 22, wherein the damper comprises a viscous damper.

24. The medicament delivery device according to claim 23, comprising a rack arranged for engagement with a toothed rotary element of the damper, such that the movement of the coupling member with respect to the carriage causes rotation of the rotary element against a damping fluid to retard the movement of the coupling member.

25. The medicament delivery device according to claim 24, wherein the rotary element is moveable with the coupling member, and wherein the rack is associated with the carriage.

26. The medicament delivery device according to claim 17, comprising a wheel that is driven for rotation with respect to the carriage by the drive mechanism, and wherein the retraction mechanism is activated upon rotation of the wheel through a pre-defined angle.

27. The medicament delivery device according to claim 26,
wherein the insertion mechanism comprises an insertion spring for biasing the carriage in the insertion direction (H),
wherein the retraction mechanism comprises a coupling arrangement for releasably coupling the insertion spring to the carriage and for decoupling the insertion spring from the carriage upon activation of the retraction mechanism;
wherein the coupling arrangement comprises a coupling member that is moveable with respect to the carriage to decouple the insertion spring from the carriage and a retaining member arranged to prevent movement of the coupling member before the activation of the retraction member and to allow movement of the coupling member upon the activation of the retraction mechanism; and
wherein the wheel comprises an actuator element for cooperation with the retaining member upon the rotation of the wheel through the pre-defined angle, thereby to cause release of the coupling member.

28. The medicament delivery device according to claim 27, wherein the retaining member comprises a lever arranged to pivot with respect to the carriage upon cooperation with the actuator element, thereby to release the coupling member.

29. The medicament delivery device according to claim 17, wherein the retraction mechanism comprises a retraction spring for driving movement of the carriage in the retraction direction to retract the cannula after the delivery of the medicament.

30. The medicament delivery device according to claim 1, wherein the cannula is substantially coaxial with the container axis (A) in a starting state of the device.

31. The medicament delivery device according to claim 30, wherein the cannula comprises a needle attached to an end of the container.

32. The medicament delivery device according to claim 31, wherein the container comprises a syringe body of a pre-filled syringe.

33. A medicament delivery device for delivery of medicament from a container into an injection site through a cannula, the device comprising:
   a contact face for placement against the injection site;
   a drive mechanism for driving a piston member of the container along a container axis (A) to expel the medicament through the cannula, the container axis (A) being substantially parallel to the contact face;
   an insertion mechanism operable to move the cannula in an insertion direction (H) to extend the cannula through an aperture in the contact face;
   a sensor for detecting if the contact face is in contact with the injection site;
   an interlock coupled to the sensor and switchable from a first state in which operation of the insertion mechanism is prevented to a second state in which operation of the insertion mechanism is possible, in response to the contact face being placed against the injection site; and
   a user-removable component configured to prevent switching of the interlock from the first state to the second state until the user-removable component has been removed.

34. The medicament delivery device according to claim 33, wherein the sensor comprises a sensing element disposed at the contact face and arranged to contact the injection site when the contact face is placed against the injection site.

35. The medicament delivery device according to claim 34, wherein the sensing element is biased to project from the contact face, and wherein the sensing element is movable into a retracted position when the contact face is placed against the injection site.

36. The medicament delivery device according to claim 34, wherein the sensing element is disposed in the aperture in the contact face, and wherein the sensing element comprises an opening to allow extension of the cannula through the aperture upon operation of the insertion mechanism.

37. The medicament delivery device according to claim 33, comprising a trigger arrangement that is moveable to operate the insertion mechanism, and wherein the interlock prevents movement of the trigger arrangement when the interlock is in the first state.

38. The medicament delivery device according to claim 37, wherein the interlock comprises a trigger blocking element for blocking the movement of the trigger arrangement.

39. The medicament delivery device according to claim 38, wherein the interlock comprises a beam member for coupling the sensor to the trigger blocking element.

40. The medicament delivery device according to claim 39, wherein the beam member is arranged to pivot upon switching of the interlock from the first state to the second state.

41. The medicament delivery device according to claim 37, wherein the trigger arrangement comprises a trigger lever arranged to pivot to operate the insertion mechanism.

42. The medicament delivery device according to claim 37, wherein the contact face comprises a base of the device, and wherein the trigger arrangement is disposed on a side wall of the device.

43. The medicament delivery device according to claim 33, wherein the user-removable component is removable along the container axis (A).

44. The medicament delivery device according to claim 33, wherein the user-removable component comprises a deshielder for removing a shield from the cannula.

45. The medicament delivery device according to claim 33, further comprising a carriage for retaining the container, the cannula and the drive mechanism, and wherein the carriage is biased for movement in the insertion direction (H) relative to the contact face upon operation of the insertion mechanism.

* * * * *